(12) United States Patent
Knaack et al.

(10) Patent No.: US 7,163,691 B2
(45) Date of Patent: Jan. 16, 2007

(54) BONE GRAFT

(75) Inventors: David Knaack, Holmdel, NJ (US); Kathy Traianedes, North Brunswick, NJ (US); Michele Diegman, Scotch Plains, NJ (US); Nanette Forsyth, Bayville, NJ (US); John Winterbottom, Jackson, NJ (US)

(73) Assignee: Osteotech, Inc., Eatontown, NJ (US)

( * ) Notice: Subject to any disclaimer, the term of this patent is extended or adjusted under 35 U.S.C. 154(b) by 488 days.

(21) Appl. No.: 10/271,140

(22) Filed: Oct. 15, 2002

(65) Prior Publication Data

US 2003/0143258 A1 Jul. 31, 2003

Related U.S. Application Data

(60) Provisional application No. 60/392,462, filed on Jun. 27, 2002, provisional application No. 60/329,156, filed on Oct. 12, 2001.

(51) Int. Cl.
*A61F 2/28* (2006.01)
(52) U.S. Cl. ............... 424/426; 523/113; 523/114; 523/115; 523/116
(58) Field of Classification Search ........... 424/426; 523/114, 115, 113, 116
See application file for complete search history.

(56) References Cited

U.S. PATENT DOCUMENTS

| | | | |
|---|---|---|---|
| 4,394,370 A | 7/1983 | Jefferies | 424/15 |
| 4,440,370 A | 4/1984 | Rood | 248/75 |
| 4,485,097 A | 11/1984 | Bell | 248/75 |
| 4,678,470 A | 7/1987 | Nashef et al. | 623/16 |
| 4,743,259 A | 5/1988 | Bolander et al. | 623/16 |
| 5,236,456 A | 8/1993 | O'Leary et al. | 623/16 |
| 5,284,655 A * | 2/1994 | Bogdansky et al. | 424/422 |
| 5,314,476 A | 5/1994 | Prewett et al. | 623/16 |
| 5,490,962 A | 2/1996 | Cima et al. | 264/22 |

(Continued)

FOREIGN PATENT DOCUMENTS

EP 0 567 391 10/1993

OTHER PUBLICATIONS

Crowe, et al., "Inhibition of Enzymic Digestion of Amylose by Free Fatty Acids in Vitro Contributes to Resistant Starch Formation", *J. Nutr.* 130(8): 2006-2008, 2000.

(Continued)

*Primary Examiner*—Carlos A. Azpuru
(74) *Attorney, Agent, or Firm*—Dorsey & Whitney LLP

(57) ABSTRACT

An improved demineralized bone matrix (DBM) or other matrix composition is provided that has been mixed with a stabilizing agent that acts as (1) a diffusion barrier, (2) a enzyme inhibitor, (3) a competitive substrate, or (4) a masking moiety. A diffusion barrier acts as a barrier so as to protect the osteoinductive factors found in DBM from being degraded by proteolytic and glycolytic enzymes at the implantation site. Stabilizing agents may be any biodegradable material such as starches, modified starches, cellulose, dextran, polymers, proteins, and collagen. As the stabilizing agents degrades or dissolves in vivo, the osteoinductive factors such as TGF-β, BMP, and IGF are activated or exposed, and the activated factors work to recruit cells from the preivascular space to the site of injury and to cause differentiation into bone-forming cells. The invention also provides methods of preparing, testing, and using the inventive improved osteodinductive matrix compositions.

1 Claim, 6 Drawing Sheets

Example of Rabbit Ulna defect

Three week in-vivo radiographs showing evidence of bone formation.

Glycerol-based formulation      Starch-based formulation

U.S. PATENT DOCUMENTS

| | | | |
|---|---|---|---|
| 5,507,813 A | 4/1996 | Dowd et al. | 623/16 |
| 5,518,680 A | 5/1996 | Cima et al. | 264/401 |
| 5,607,269 A | 3/1997 | Dowd et al. | 409/134 |
| 5,807,437 A | 9/1998 | Sachs et al. | 118/688 |
| 6,326,018 B1 | 12/2001 | Gertzman et al. | 424/423 |

OTHER PUBLICATIONS

Edwards, et al., "Osteoinduction of Human Demineralized Bone: Characterization in a Rat Model", *Clinical Orthopeadics & Rel. Res.* 357: 219-228, 1998.

Glowacki, et al., "Demineralized Bone Implants", *Clinics in Plastic Surgery*, 12(2): 233-241, 1985.

Kubler, et al., "Erstes BMP-Analog Mit Osteoinduktiven Eigenschaften", *Mund Kiefer Gesichtschir.* 3 Suppl. 1: S134-S139, 1999.

Kubler, et al., "Allogenic Bone and Cartilage Morphogenesis", *J. Craniomaxillofac. Surg.* 19(7): 283-288, 1991.

Kubler, et al., "Einfluss Unterschiedlicher Faktoren Auf Die Knochenbildenden Eigenschaften Von Rekombinanten BMPs", *Mund. Kiefer Gesichtschir.* 4 Supp.2: S465-S469, 2000.

Mulliken, et al., "Fate of Mineralized and Demineralized Osseous Implants in Cranial Defects" *Calcified. Tissue Int.* 33: 71-76, 1981.

Neigal, et al., Use of Demineralized Bone Implants in Orbital and Craniofacial *Opthal. Plast. Reconstr. Surg.* 12: 108-120, 1996.

Ray, et al., "Preliminary Report of an Experimental Study", *J. Bone Joint Surgery*, 39A: 1119,-1128 1957.

Russell, et al., "Clinical Utility of Demineralized Bone Matrix for Osseous Defects, Arthrodesis, and Reconstruction: Impact of Processing Techniques and Study Methodology", *Orthopaedics*, 22(5): 524-531, 1999.

Ueland, et al., "Increased Cortical Bone Content of Insulin-Like Growth Factors in Acromegalic Patients" *J. Clin. Endocrinol Metab.* 84(1): 123-127, 1999.

Urist, "Bone: Formation by Autoinduction", *Science*, 150: 893-899, 1965.

Whiteman, et al., "Demineralized Bone Powder -Clinical Applications for Bone Defects of the Hand" *J. Hand. Surg.* 18B: 487-490, 1993.

Whittaker, et al., "Matrix Metalloproteinases and Their Inhibitors—Current Status and Future Challenges", *Celltransmissions*, 17(1): 3-14.

Xiaobo, et al., "Experimental and Clinical Investigations of Human Insoluble Bone Matrix Gelatin", *Clin. Orthrop.* 293: 360-365, 1993.

Zhang, et al., "A Quantitative Assessment of Osteoinductivity of Human Demineralized Bone Matrix", *J. Periodontol.* 68(11): 1076-1084, 1997.

* cited by examiner

Example of Rabbit Ulna defect
Figure 1. Three week in-vivo radiographs showing evidence of bone formation.
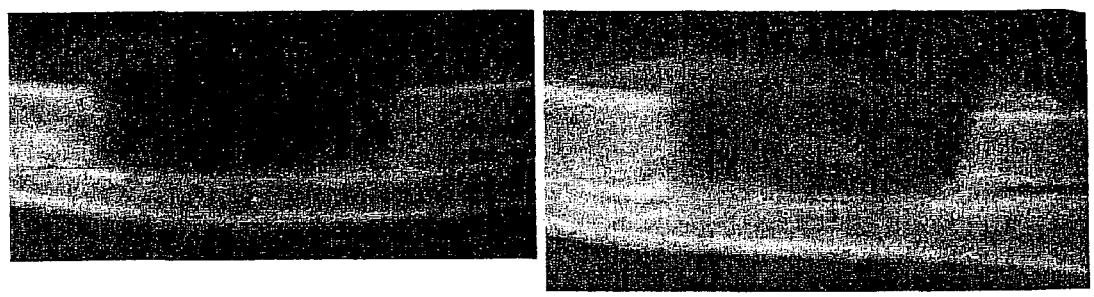
Glycerol-based formulation         Starch-based formulation
Figure 2. Six week X-rays or faxitron images
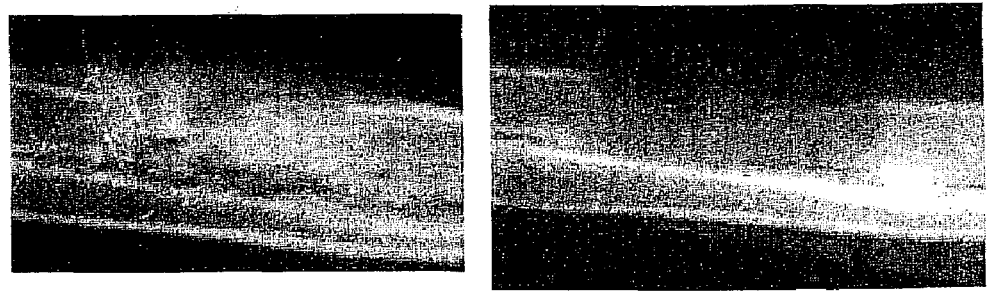
Autograft         Glycerol-based formulation
 
Empty
Starch-based formulation Devitalized (alone)　　　　　Devitalized+10ug hrhBMP-2x
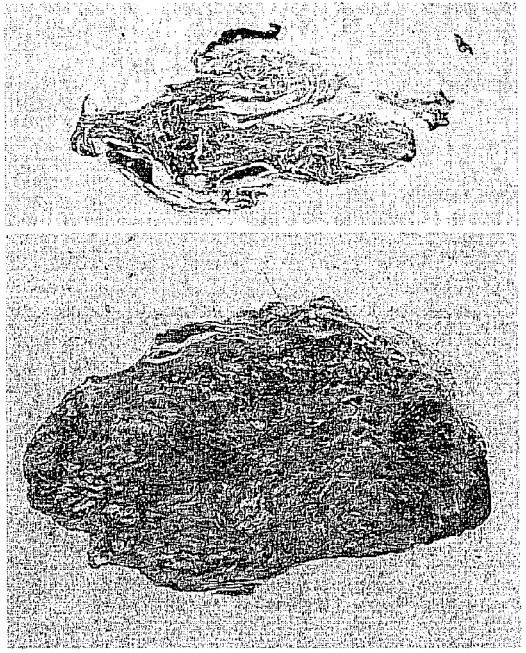 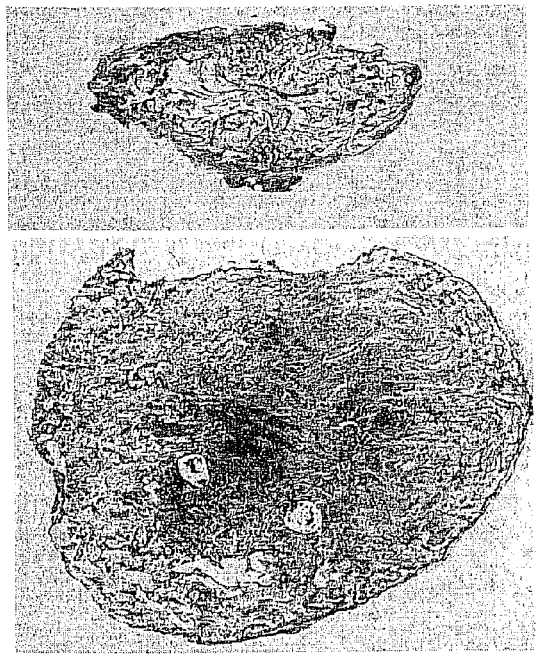
DBF Matrix (alone)　　　　　DBF Matrix+10ug hrhBMP-2x
FIGURE 4

BONE GRAFT

RELATED APPLICATIONS

The present application claims priority to co-pending provisional applications U.S. Ser. No. 60/392,462, entitled "Improved Bone Graft", by Knaack et al., filed Jun. 27, 2002, and U.S. Ser. No. 60/329,156, entitled "Osteoinductive Composition" by Traianedes et al., filed Oct. 12, 2001, each of which is incorporated herein by reference in its entirety.

BACKGROUND

The rapid and effective repair of bone defects caused by injury, disease, wounds, surgery, etc., has long been a goal of orthopaedic surgery. Toward this end, a number of compositions and materials have been used or proposed for use in the repair of bone defects. The biological, physical, and mechanical properties of the compositions and materials are among the major factors influencing their suitability and performance in various orthopaedic applications.

Autologous cancellous bone ("ACB") is considered the gold standard for bone grafts. ACB is osteoinductive, is non-immunogenic and, by definition, has all of the appropriate structural and functional characteristics appropriate for the particular recipient. Unfortunately, ACB is only available in a limited number of circumstances. Some individuals lack ACB of appropriate dimensions and quality for transplantation. Moreover, donor site morbidity can pose serious problems for patients and their physicians.

Much effort has been invested in the identification or development of alternative bone graft materials. Demineralized bone matrix ("DBM") implants have been reported to be particularly useful (see, for example, U.S. Pat. Nos. 4,394,370; 4,440,750; 4,485,097; 4,678,470; and 4,743,259; Mulliken et al., *Calcif. Tissue Int.* 33:71, 1981; Neigel et al., *Opthal. Plast. Reconstr. Surg.* 12:108, 1996; Whiteman et al., *J. Hand. Surg.* 18B:487, 1993; Xiaobo et al., *Clin. Orthop.* 293:360, 1993; each of which is incorporated herein by reference). Demineralized bone matrix is typically derived from cadavers. The bone is removed aseptically and/or treated to kill any infectious agents. The bone is then particulated by milling or grinding and then the mineral component is extracted (e.g., by soaking the bone in an acidic solution). The remaining matrix is malleable and can be further processed and/or formed and shaped for implantation into a particular site in the recipient. Demineralized bone prepared in this manner contains a variety of components including proteins, glycoproteins, growth factors, and proteoglycans. Following implantation, the presence of DBM induces cellular recruitment to the site of injury. The recruited cells may eventually differentiate into bone forming cells. Such recruitment of cells leads to an increase in the rate of wound healing and, therefore, to faster recovery for the patient.

Current DBM formulations have various drawbacks. First, while the collagen-based matrix of DBM is relatively stable, the active factors within the DBM matrix are rapidly degraded. The osteogenic activity of the DBM may be significantly degraded within 24 hours after implantation, and in some instances the osteogenic activity may be inactivated within 6 hours. Therefore, the factors associated with the DBM are only available to recruit cells to the site of injury for a short time after transplantation. For much of the healing process, which may take weeks to months, the implanted material may provide little or no assistance in recruiting cells.

In addition to the active factors present within the DBM, the overall structure of the DBM implant is also believed to contribute to the bone healing capabilities of the implant.

SUMMARY OF THE INVENTION

The present invention provides improved demineralized bone matrix ("DBM") compositions, related methods for preparing and using the inventive compositions, and kits containing the inventive compositions. The invention encompasses the recognition that the fast reduction in osteoinductive capabilities observed with previously available DBM compositions may result from (1) degradation of osteoinductive agents, for example, as a result of proteases, sugar-degrading enzymes, or other enzymes present in the host or the DBM itself, (2) diffusion of osteoinductive agents out of the DBM; and/or (3) reduced activation of osteoinductive agents in the DBM. The present invention therefore provides DBM compositions in which osteoinductive agents are protected from degradation and/or from diffusion out of the composition. The present invention may also include activation of the osteoinductive factors found in the DBM, for example, in a controlled time release manner. In some embodiments, the invention also provides improved shape-retaining characteristics contributing to the overall efficacy of the DBM compositions. Also, in some embodiments, the inventive DBM composition can be used as a delivery device to administer bioactive agents.

Protection of the active factors within the DBM is provided using (1) diffusion barriers (e.g., polymers, starch), (2) enzyme inhibitors (e.g., protease inhibitors), (3) competitive substrates, and/or (4) masking moieties. Certain embodiments of the invention provide DBM compositions comprising a stabilizing agent such as a polymer or other factor (e.g., protease inhibitors). Preferably, the polymer as a diffusion barrier is metabolized over time, so that the osteoinductive agents are unmasked and/or released from the DBM composition over time, or retarded in their degradation rate. Diffusion barriers of the invention may also work through alternative means by decreasing the diffusion of the activating enzymes to the factors present in the DBM composition. Preferably, such unmasking, release, controlled release, or controlled degradation occurs over a period longer than several hours, preferably longer than a day to several days, and possibly lasting weeks or even months. In certain preferred embodiments, the rates of degradation, release, and activation are balanced to yield a DBM composition with the desired level of osteoinductivity over time. Inventive compositions containing a stabilizing agent typically show osteoinductive activity for longer periods of time than is seen with comparable compositions lacking the stabilizing agent.

In some embodiments of the invention, the stabilizing agent may comprise a polymer, such as a biodegradable polymer (e.g., that inhibits or delays diffusion of osteoinductive agents out of the DBM composition, and/or blocks access of degrading and/or activating enzymes to the osteoinductive agents). Examples of biodegradable polymers include starches, dextrans, cellulose, poly-esters, proteins, polycarbonates, polyarylates, and PLGA. Preferably the polymers are biocompatible and biodegradable.

In other embodiments, inventive DBM compositions may include and/or be treated with agents that inhibit the activity of one or more activating enzymes, proteases, or glycosidases. Such inhibitory agents are expected to reduce the activity of specific enzymes (whether derived from the host or from the DBM) that would otherwise interact with osteoinductive agents or other active agents in the DBM, thereby reducing osteoinductivity or wound healing. Alternatively or additionally, inventive DBM compositions may include inhibitory agents presented in a time-release formulation (e.g., encapsulated in a biodegradable polymer). In the case of activating enzymes (i.e., enzymes which lead to the release, presentation, or creation of osteoinductive factors), inhibitory agents that reduce the activity of activating enzymes preferably lead to increased osteoinductivity over an extended period of time rather than just a burst just after implantation.

Some embodiments of the present invention comprise DBM compositions particularly formulated to control or adjust the rate by which the composition, or portions thereof, lose osteoinductivity. To give but one example, DBM compositions may be prepared from multiple different DBM preparations, each of which contains DBM particles of different size and/or including different amounts or types of stabilizing agents. For instance, DBM preparations or powders may be prepared that have varying half-lives as determined by changing, for instance, the nature or amount of a stabilizing polymer, the extent of cross-linking of the polymer, the thickness of a stabilizing coating, the size of the particles, the amount of inhibitors of activating or degradatory enzymes, etc. Adjusting the amounts or locations of the different DBM preparations within the overall inventive DBM composition can modify the characteristics of part or all of the inventive composition. In this manner, for example, the formulation could be customized to the patient, type of injury, site of injury, length of recovery, underlying disease, etc.

In another aspect, the present invention provides methods of preparing inventive improved DBM compositions. For instance, the present invention provides methods of formulating an improved DBM composition for a particular site or injury.

The present invention also provides systems and reagents for preparing and applying DBM grafts, as well as systems and reagents for treating bone defects using DBM implants. For example, the DBM composition may be provided as a paste in a delivery device such as a syringe. Preferably, the DBM composition is sterile and is packaged so that it can be applied under sterile conditions (e.g., in an operating room).

The present invention further provides a system for characterizing DBM composites, and for identifying and preparing DBM-containing materials with improved properties.

Furthermore, the present invention provides a system for delivering bioactive agents, such as growth factors (e.g., bone morphogenic proteins, growth factors, hormones, angiogenic factors, cytokines, interleukins, osteopontin, osteonectin), to a host animal. The use of a DBM composition as a delivery vehicle for bioactive agents provides for the unexpected result of an improved healing response to the implant without the need to administer separately the bioactive agent. A problem with the introduction of the bioactive agent at the site is that it is often diluted and redistributed during the healing process by the circulatory systems (e.g., blood, lymph) of the recipient before complete healing has occurred. A solution to this problem of redistribution is to affix the bioactive components to the osteoimplant. Some preferred bioactive agents that can be delivered using a DBM composition include agents that promote the natural healing process, i.e., resorption, vascularization, angiogenesis, new growth, etc. A list of biological agents that may be delivered using inventive DBM compositions is included as Appendix A. In preferred embodiments of this aspect of the invention, an inventive composition is provided in which DBM, together with a stabilizing agent, is used to deliver the biologically active agent. It is expected that the stabilizing agent will protect the biologically active agent from degradation, and therefore will extend its active life after delivery into the recipient animal. In certain embodiments, the bioactive agent is an osteoinductive agent, and in certain embodiments, the DBM may be used to deliver more than one bioactive agent, preferably more than two, and more preferably sometimes more than three bioactive agents. The bioactive agent may be associated with the DBM. For example, the bioactive agent may be associated with the DBM through electrostatic interactions, hydrogen bonding, pi stacking, hydrophobic interactions, van der Waals interactions, etc. In certain embodiments, the bioactive agent is attached to the DBM through specific interactions such as those between a receptor and its ligand or between an antibody and its antigen. In other embodiments, the bioactive agent is attached to the DBM through non-specific interactions (e.g., hydrophobic interactions).

BRIEF DESCRIPTION OF THE DRAWING

FIG. 1. Three week in-vivo radiographs showing evidence of bone formation.

FIG. 2. Six week x-rays or faxitron images.

A. The vascularity and marrow cellularity increased on active DBF in a dose-dependent fashion with increasing concentrations of hrhBMP-2x, which was not evident in the devitalized group. The wild type rhBMP-2 at the 5 µg dose was similar to the hybrid BMP.

B. The residual DBF remained a significant part of the nodule in each of the devitalized groups. The residual DBF dose-dependently deceased with increasing amounts of hrh-BMP-2x in the active DBF group. The wild type rhBMP-2 was not as effective in remodeling the DBF as the hrhBMP-2x.

FIG. 4. Comparison of untreated and hrhBMP-2x treated devitalized and active DBF matrix.

Devitalized: Only residual DBF present with no bone formation elements evident.

Devitalized+10 µg hrhBMP-2x: New bone lining residual bone; extensive immature marrow with many adipocytes throughout nodule; extensive bone formation at outer edge of nodule but no rim present.

DBF: Rim of residual DBF present with extensive chondrocytes, bone, and some marrow formation.

DBF+10 µg hrhBMP-2x: Thin rim of mature new bone with extensive bone formation through out nodule with very little residual DBF remaining at center; extensively vascularized with well developed hematopoietic marrow present.

Figure 3A:
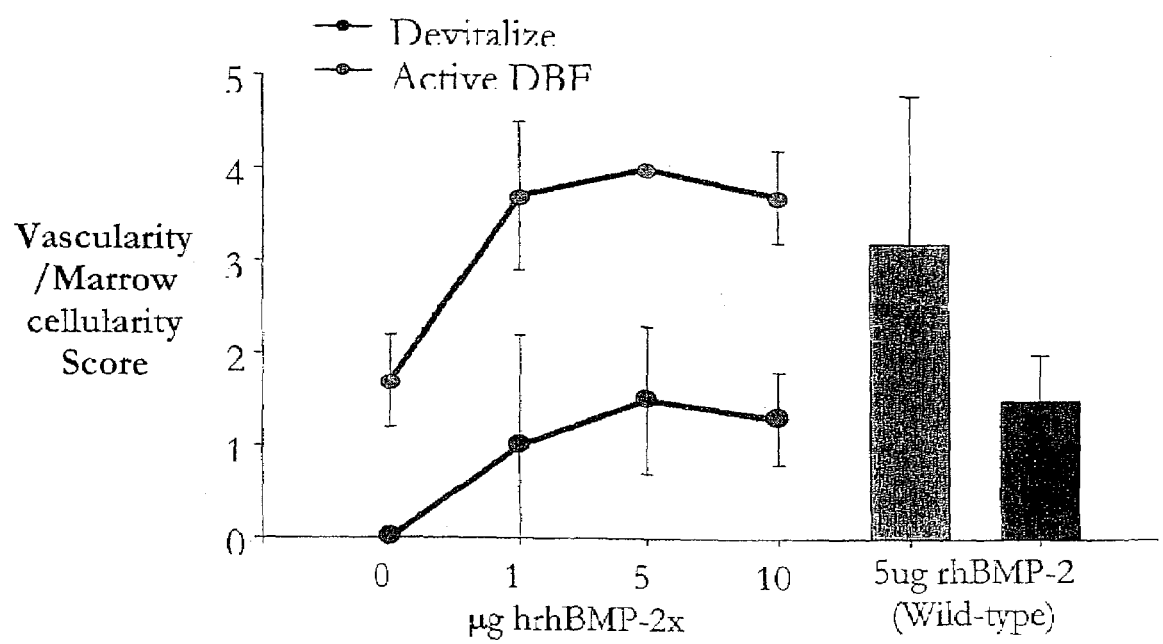
FIG. 3. Qualitative evaluation of Vascularity (A) and Residual Demineralized Bone Fiber (DBF) (B).
Figure 3B:
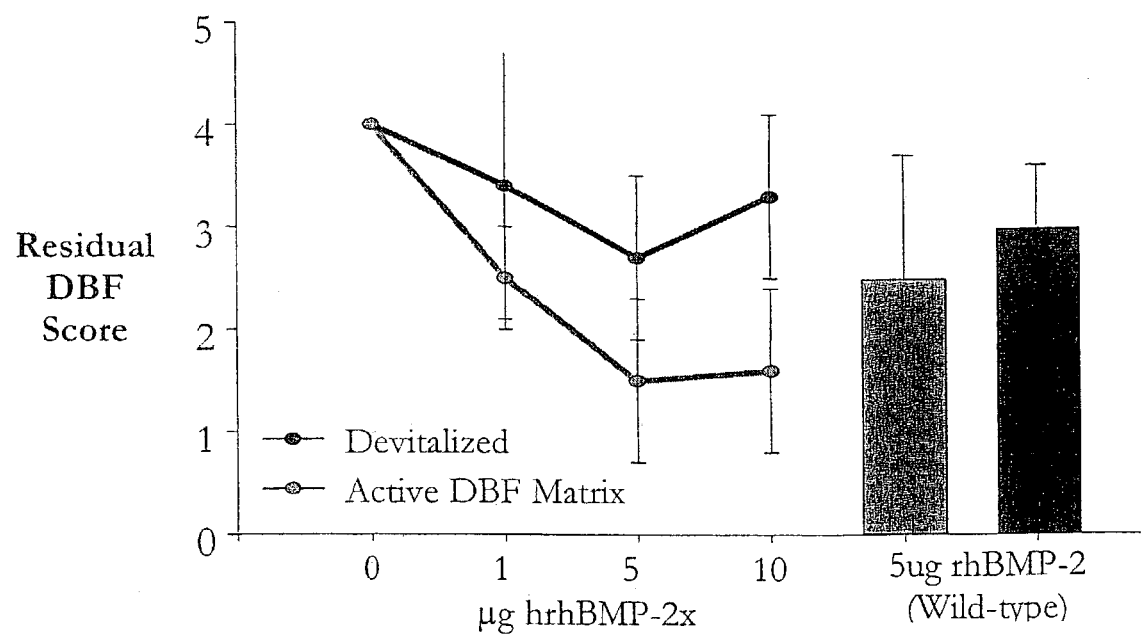
Figure 5:
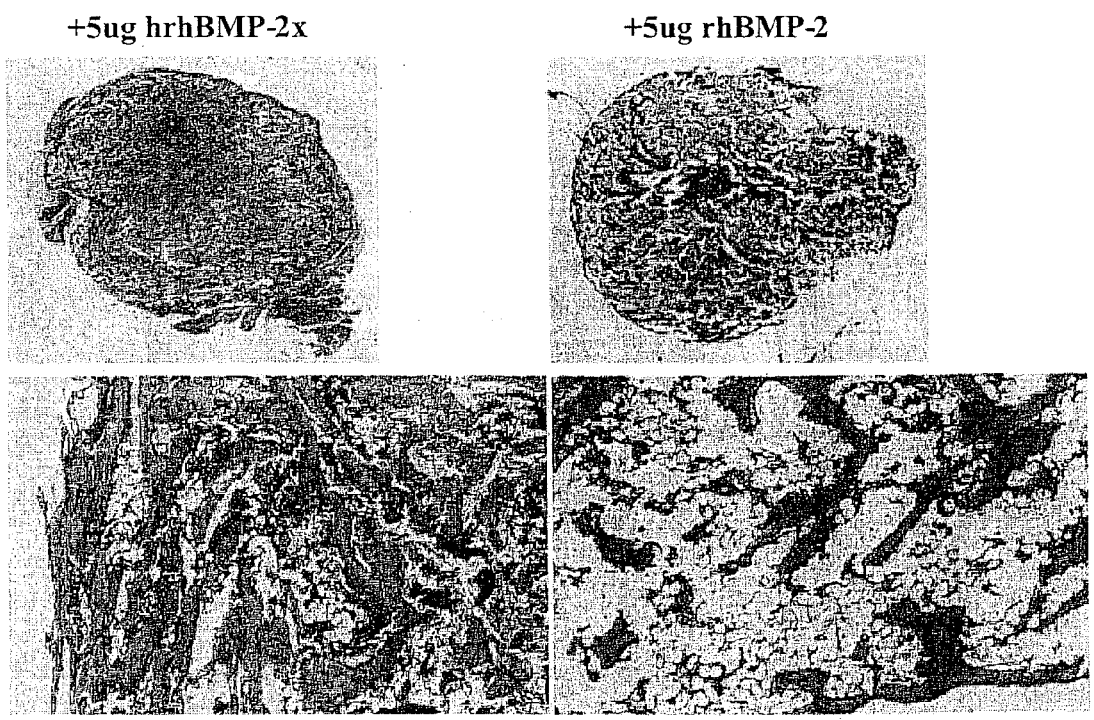

FIG. 5. Histological comparison of hrhBMP-2x and wild type rhBMP-2 treated DBF matrix. There was significant bone formation in the hrhBMP-2x treated group compared to the rhBMP-2 group as evidenced by fewer spicules of bone and an extensive fatty marrow in the wild type group. A more developed, blood marrow was evident in the hybrid rhBMP-2x group.

Figure 6:
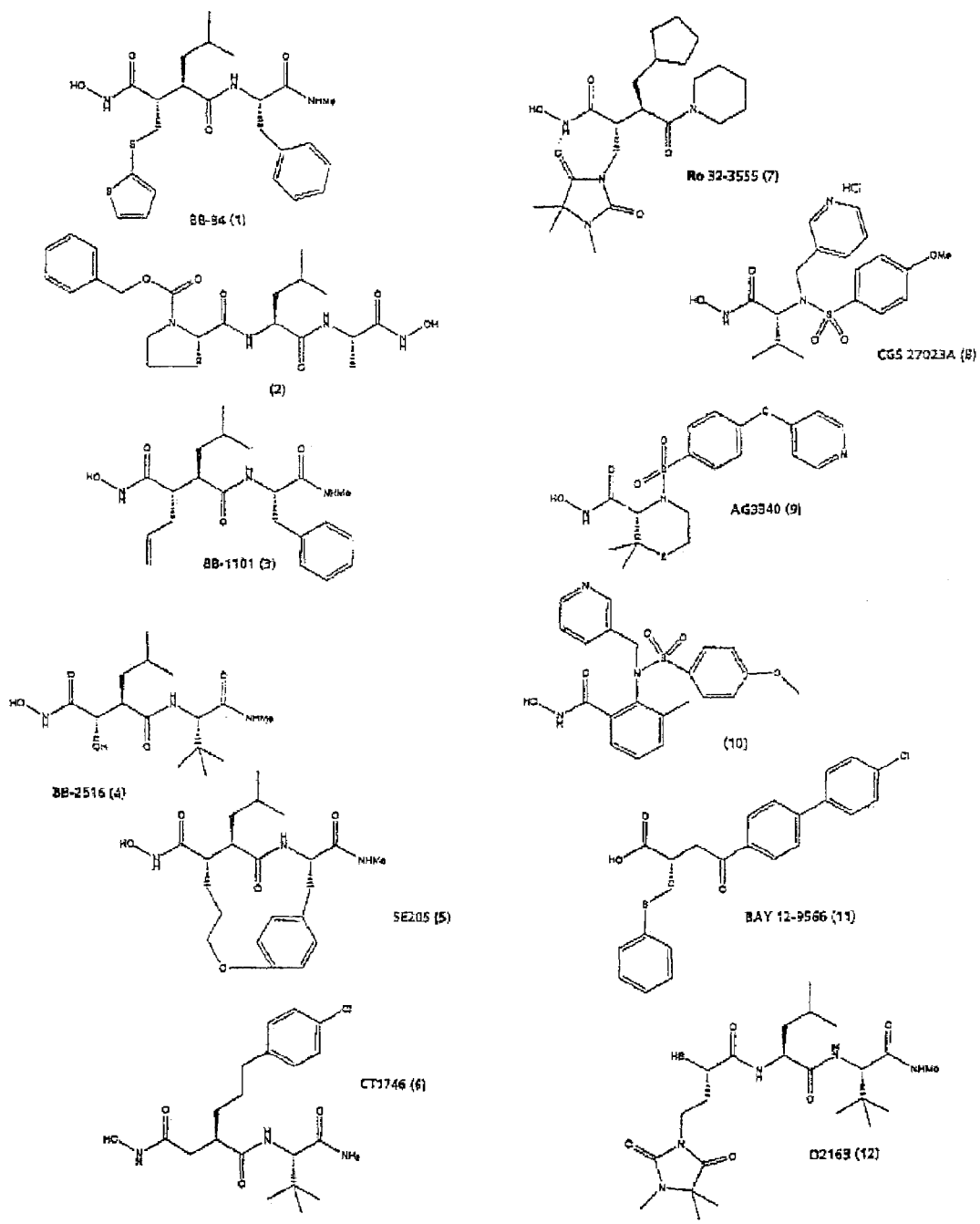

FIG. 6. Chemical structure of some examples of matrix metalloproteinase inhibitors.

DEFINITIONS

Associated with: A stabilizing agent or other chemical entity is associated with DBM or other osteogenic matrix according to the present invention if it is retained by the implant long enough to significantly enhance the osteoinductivity of the implant. Specific examples include 1) not freely diffusible from the DBM as determined in in vitro diffusion assays in simulated body fluids; and/or 2) has an extended half-life in the DBM as compared with free in solution. In some embodiments, associations are covalent; in others they are non-covalent. Examples of non-covalent interactions include electrostatic interactions, hydrogen bonding, hydrophobic interactions, and van der Waals interactions. For instance, a bioactive agent may be rendered associated with a DBM or other inventive matrix by virtue of a polymeric stabilizing agent that restrains diffusion of the bioactive agent from the matrix. Alternatively or additionally, the bioactive agent may be rendered associated with a DBM by virtue of a physical interaction with one or more entities that are themselves associated with the DBM. For example, the BMP-2 in Example 12 is considered to be associated with the DBM, and the BMP-2x is considered to be more closely associated with the DBM than the BMP-2.

Demineralized bone activity refers to the osteoinductive activity of demineralized bone.

Demineralized bone matrix, as used herein, refers to any material generated by removing mineral material from living bone tissue. In preferred embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the invention.

Diffusion barrier refers to any material, coating, film, or substance that decreases the rate of diffusion of a substance from one side of the barrier to the other side, and more specifically, from outside to in or vice versa. The diffusion barrier in certain embodiments may be a polymer including proteins, polysaccharides, cellulose, man-made polymer, PLGA, etc. that prevents the diffusion of activating agents (including water, enzymes, etc.) and/or degradatory enzymes into the DBM composition. The diffusion barrier may also prevent the movement of osteoinductive factors out of the DBM composition. In certain embodiments, the diffusion barrier is biodegradable leading to the degradation, activation, or release of osteoinductive factors over an extended period of time.

Matrix, as used herein, refers to a natural or non-natural substantially solid vehicle capable of association with at least one growth factor for delivery to an implant site. The matrix may be completely insoluble or may be slowly solubilized after implantation. Following implantation, preferred matrices resorb or degrade, remaining substantially intact for at least one to seven days, most preferably for two or four weeks or longer and often longer than 60 days. Growth factors may be endogenously present on the matrix as in the case of most demineralized bone, or they may be exogenously added to the matrix. Matrices may also comprise combinations of endogenous and exogenous growth factors. The matrix may be in particulate or fiber form, or may be monolithic. The matrix may comprise a number of materials and forms in combination such as fibers and particles. In one preferred embodiment, the matrix is comprised of heat pressed demineralized bone fibers. In other embodiments, the matrix comprises resorbable plastic polymers such as those described below as suitable for use as diffusion barriers. In other preferred embodiments, a particulated amorphous calcium phosphate is used as the matrix in association with an adsorbed growth factor such as a BMP. More specifically BMP-2 or BMP-4 or derivatives thereof. Still other matrix embodiments requiring the addition of an exogenous growth factor include, but are not limited to, particulated ceramics, preferably calcium sulphates or calcium phosphates. The most preferred matrices are calcium phosphates, the preparation of which is well known to practitioners in the art (see, for example, Driessens et al. "Calcium phosphate bone cements" Wise, D. L., Ed. *Encyclopedic Handbook of Biomaterials and Bioengineering, Part B, Applications* New York: Marcel Decker; Elliott *Structure and Chemistry of the Apatites and Other Calcium Phosphates* Elsevier, Amsterdam, 1994; each of which is incorporated herein by reference). Calcium phosphate matrices include, but are not limited to, dicalcium phosphate dihydrate, monetite, tricalcium phospate, tetracalcium phosphate, hydroxyapatite, nanocrystalline hydroxyapatite, poorly crystalline hydroxyapatite, substituted hydroxyapatite, and calcium deficient hydroxyapatites.

Osteoinductive, as used herein, refers to the quality of being able to stimulate bone formation. Any material that can induce the formation of ectopic bone in the soft tissue of an animal is considered osteoinductive. For example, most osteoinductive materials induce bone formation in athymic rats when assayed according to the method of Edwards et al. ("Osteoinduction of Human Demineralized Bone: Characterization in a Rat Model" *Clinical Orthopeadics & Rel. Res.*, 357:219–228, December 1998; incorporated herein by reference). Osteoinductivity in some instances is considered to occur through cellular recruitment and induction of the recruited cells to an osteogenic phenotype. Osteoinductivity may also be determined in tissue culture as the ability to induce an osteogenic phenotype in culture cells (primary, secondary, or explants) It is advisable to calibrate the tissue culture method with an in vivo ectopic bone formation assay as described by Zhang et al. "A quantitative assessment of osteoinductivity of human demineralized bone matrix" *J. Periodontol.* 68(11):1076–84, November 1997; incorporated herein by reference. Calibration of the in vitro assays against a proven in vivo ectopic bone formation model is critical because the ability of a compound to induce an apparent "osteogenic" phenotype in tissue culture may not always be correlated with the induction of new bone formation in vivo. BMP, IGF, TGF-$\beta$, parathyroid hormone (PTH), and angiogenic factors are only some of the osteoinductive factors found to recruit cells from the marrow or perivascular space to the site of injury and then cause the differentiation of these recruited cells down a line responsible for bone formation. DBM isolated from either bone or dentin have both been found to be osteoinductive materials (Ray et al., "Bone implants" *J. Bone Joint Surgery* 39A:1 119, 1957; Urist, "Bone: formation by autoinduction" *Science* 150:893, 1965; each of which is incorporated herein by reference).

Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%–25% of implant involved in new bone formation; "2" represents 26–50% of implant involved in new bone formation; "3" represents 51%–75% of implant involved in new bone formation; and "4" represents >75% of implant involved in new bone formation. In most instances, the score is assessed 28 days after implantation. However, for the improved inventive formulations, particularly those with osteoinductivity comparable to the BMPs, the osteoinductive score may be obtained at earlier time points such as 7, 14, or 21 days following implantation. In these instances it is important to include a normal DBM control such as DBM powder without a carrier, and if possible, a positive control such as BMP. Occasionally osteoinductivity may also be scored at later timepoints such as 40, 60, or even 100 days following implantation. Percentage of osteoinductivity refers to an osteoinductivity score at a given time point expressed as a percentage of activity, of a specified reference score.

Particle or fibers refers to a preparation of DBM, DBM compositions, or bone sample that has been milled, ground, pulverized, or otherwise reduced to a particulate form. The size of the particles or fibers is typically greater than 50 microns, preferably greater than 75 microns, more preferably greater than 100 microns, and most preferably greater than 150 microns. These dimensions refer to average particle diameter for more spherical-like particles, and for particles of other shapes except where specifically indicated it refers to the smallest cross-sectional dimension of the particle. In certain embodiments, the composition may include even larger sized particles, preferably greater than 1 mm, greater than 1.5 mm, or most preferably greater than 2 mm in their largest dimension. The particles or fibers may be of any shape including wedges, rods, spheres, cubes, discs, ovals, irregularly shaped, etc. For example, in certain embodiments, the particles may be wedge-shaped and be approximately 2 mm in their largest dimension and 100 microns or less in another dimension. The particles or fibers may be sieved or sorted in order to collect particles of a particular size. These particles or fibers may be mixed with a solution, slurry, deformable solid, or liquid to form a paste to be used in administering or applying the graft of DBM, inventive DBM composition, or bone sample. Preferred methods of particle or fiber preparation are disclosed in issued U.S. Pat. Nos. 5,607,269; 5,236,456; 5,284,655; 5,314,476; and 5,507,813; each of which is incorporated herein by reference.

Polysaccharide, as used herein, refers to any polymer or oligomer of carbohydrate residues. The polymer may consist of anywhere from two to hundreds to thousands of sugar units. Polysaccharides may be purified from natural sources such as plants or may be synthesized de novo in the laboratory. Polysaccharides isolated from natural sources may be modified chemically to change their chemical or physical properties (e.g., phosphorylated, cross-linked). Polysaccharides may also be either straight or branchchained. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, and fructose. Glycosaminoglycans are also considered polysaccharides.

Protease inhibitors, as used herein, are chemical compounds capable of inhibiting the enzymatic activity of protein cleaving enzymes (i.e., proteases). The proteases inhibited by these compounds include serine proteases, acid proteases, metalloproteases (examples of some matrix metalloprotease inhibitors are shown in FIG. 6), carboxypeptidase, aminopeptidase, cysteine protease, etc. The protease inhibitor may act specifically to inhibit only a specific protease or class of proteases, or it may act more generally by inhibiting most if not all proteases. Preferred protease inhibitors are protein or peptide based and are commercially available from chemical companies such as Aldrich-Sigma. Protein or peptide-based inhibitors which adhere to the DBM (or calcium phosphate or ceramic carrier) are particularly preferred as they remain associated with the matrix providing a stabilizing effect for a longer period of time than freely diffusible inhibitors. Examples of protease inhibitors include aprotinin, 4-(2-aminoethyl)benzenesulfonyl fluoride (AEBSF), amastatin-HCl, alpha1-antichymotrypsin, antithrombin III, alpha1-antitrypsin, 4-aminophenylmethane sulfonyl-fluoride (APMSF), arphamenine A, arphamenine B, E-64, bestatin, CA-074, CA-074-Me, calpain inhibitor I, calpain inhibitor II, cathepsin inhibitor, chymostatin, diisopropylfluorophosphate (DFP), dipeptidylpeptidase IV inhibitor, diprotin A, E-64c, E-64d, E-64, ebelactone A, ebelactone B, EGTA, elastatinal, foroxymithine, hirudin, leuhistin, leupeptin, alpha2-macroglobulin, phenylmethylsulfonyl fluoride (PMSF), pepstatin A, phebestin, 1,10-phenanthroline, phosphoramidon, chymostatin, benzamidine HCl, antipain, epsilon-aminocaproic acid, N-ethylmaleimide, trypsin inhibitor, 1-chloro-3-tosylamido-7-amino-2-heptanone (TLCK), 1-chloro-3-tosylamido-4-phenyl-2-butanone (TPCK), trypsin inhibitor, and sodium EDTA.

A peptide or protein, according to the present invention, comprises a string of at least two amino acids linked together by peptide bonds. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc.

Stabilizing agent is any chemical entity that, when included in an inventive composition comprising DBM and/or a growth factor, enhances the osteoinductivity of the composition as measured against a specified reference sample. In most cases, the reference sample will not contain the stabilizing agent, but in all other respects will be the same as the composition with stabilizing agent. The stabilizing agent also generally has little or no osteoinductivity of its own and works either by increasing the half-life of one or more of the active entities within the inventive composition as compared with an otherwise identical composition lacking the stabilizing agent, or by prolonging or delaying the release of an active factor. In certain embodiments, the stabilizing agent may act by providing a barrier between proteases and sugar-degrading enzymes thereby protecting the osteoinductive factors found in or on the matrix from degradation and/or release. In other embodiments, the stabilizing agent may be a chemical compound that inhibits the activity of proteases or sugar-degrading enzymes. In a preferred embodiment, the stabilizing agent retards the access of enzymes known to release and solubilize the active factors. Half-life may be determined by immunolgical or enzymatic assay of a specific factor, either as attached to the matrix or extracted there from. Alternatively, measurement of an increase in osteoinductivity half-life, or measurement of the enhanced appearance of products of the osteoinductive process (e.g., bone, cartilage or osteogenic cells, products or indicators thereof) is a useful indicator of stabilizing effects for an enhanced osteoinductive matrix composition. The measurement of prolonged or delayed appearance of a strong osteoinductive response will generally be indicative of an increase in stability of a factor coupled with a delayed unmasking of the factor activity.

Targeting agent is any chemical entity that, when included in an inventive compositions, will direct the composition to a particular site or cause the inventive composition to remain in a particular site within the recipient's body. A targeting agent may be a small molecule, peptide, protein, biological molecule, polynucleotide, etc. Typical targeting agents are antibodies, ligands of known receptors, and receptors. These targeting agents may be associated with the inventive composition through covalent or non-covalent interactions so that the inventive composition is directed to a particular tissue, organ, injured site, or cell type.

DESCRIPTION OF CERTAIN PREFERRED EMBODIMENTS

As described herein, the present invention provides compositions and methods relating to improved DBM or synthetic growth factor containing compositions. Below, certain aspects of preferred embodiments of the invention are described in more detail and with reference to the Figures of the Drawing. Those of ordinary skill will appreciate that a variety of embodiments or versions of the invention are not specifically discussed below but are nonetheless within the scope of the present invention, as defined by the appended claims.

DBM is comprised principally of proteins and glycoproteins, collagen being the primary protein substituent of DBM. While collagen is relatively stable, being degraded only by the relatively rare collagenase enzymes, the other proteins and active factors present in DBM are quickly degraded by enzymes present in the host. These host-derived enzymes include proteases and sugar-degrading enzymes (e.g., endo- and exo-glycosidases, glycanases, glycolases, amylase, pectinases, galacatosidases, etc.). Many of the active growth factors responsible for the osteoinductive activity of DBM exist in cryptic form, in the matrix until activated. Activation can involve the change of a pre or pro function of the factor, or release of the function from a second factor or entity which binds to the first growth factor. The instant invention alters the time course over which the active factors present in DBM can exert their osteoinductive activity either by 1) slowing the degradation of the active factors present in DBM, thereby allowing them longer residence time as active moieties, or 2) prolonging the release of one or more active factors from the implant, or 3) altering the kinetics of activation of one or more cryptic factors. The instant invention increases the effective osteoinductivity of the DBM composition by (1) altering the kinetics of activation of cryptic factors, (2) altering the delivery and/or release of active factor from the matrix, and/or (3) reducing proteolytic degradation of the active factor within or as they are released from the DBM composition. Increased bone formation presumably occurs through the recruitment of more cells into the osteogenic phenotype.

The instant invention provides four approaches to the protection of active factors from degradation by either host-derived or endogenous enzymes. Factors to be protected may be endogenous to DBM preparations or factors added to either DBM or synthetic matrix compositions. Protection is provided through the use of a) diffusion barriers, b) enzyme inhibitors, c) competitive substrates, and/or d) masking moieties. These same four approaches may be used to control the activation and/or release of osteoinductive factors in cryptic form. For example, diffusion barriers or activating enzyme inhibitors prevent activating enzyme from reaching the cryptic factors or from acting upon the cryptic factors. Preferably, degradation, release, and activation of active factors within the DBM composition is balanced to yield a desired osteoinductivity profile over time.

Demineralized Bone Matrix

DBM preparations have been used for many years in orthopaedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. Osteoconduction occurs if the implanted material serves as a scaffold for the support of new bone growth. Osteoconduction is particularly significant when bone growth is desired across a large or "critical size" defect, across which bone healing would proceed only slowly or not at all. It is generally believed that the osteoconductive properties of DBM preparations are provided by the actual shape and coherence of the implant. Thus DBM compositions comprising entangled fibers tend to have superior osteoconductive properties as compared to less fibrous, more granular preparations. Stabilizing agents which tend to preserve the shape and/or coherence of the DBM substituent can lead to better bone forming properties.

The osteoinductive effect of implanted DBM compositions is thought to result from the presence of active growth factors present on the isolated collagen-based matrix. These factors include members of the TGF-$\beta$, IGF, and BMP protein families. Particular examples of osteoinductive factors include TGF-$\beta$, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

Any of a variety of demineralized bone matrix preparations may be utilized in the practice of the present invention. DBM prepared by any method may be employed including particulate or fiber-based preparations, mixtures of fiber and particulate preparations, fully or partially demineralized preparations, mixtures of fully and partially demineralized preparations, including surface demineralized preparations as described by Gertzman et al. (U.S. Pat. No. 6,326,018, issued Dec. 4, 2001; incorporated herein by reference). Preferred DBM compositions are described by Dowd et al., U.S. Pat. No. 5,507,813, which is incorporated herein by reference. Also useful are DBM preparations comprising additives or carriers such as polyhydroxyl compounds, polysaccharides, glycosaminoglycan proteins, nucleic acids, polymers, polaxomers, resins, clays, calcium salts, and/or derivatives thereof.

In certain embodiments, the DBM material utilized to formulate inventive compositions has greater than 50%, preferably greater than 75%, more preferably greater than 80%, 85%, 90%, or 95% and most preferably greater than 98% of the calcium phosphate removed. The bone used in creating the DBM may be obtained from any source of living or dead tissue. Often, it will be preferred that the source of bone be matched to the eventual recipient of the inventive composition. At a minimum, it is often desirable that the donor and recipient are of the same species, though even xenogenic sources are permitted.

Once a bone sample is obtained, it is milled, ground, pulverized, or otherwise reduced to particulate form. In preferred embodiments, the particles will be greater than 75 microns in their minimum dimension, more preferably greater than 100 microns, and more preferably greater than 150 microns. However, it should be noted that one method of the preferred invention is to stabilize implants containing particles less than 100 microns in any dimension and potentially even less than 75 microns. Particles of 75 microns or less, following demineralization, are known to have limited or no osteoinductivity, and aspects of the present invention may be used to enhance the activity of these small size particles as well. For preparations employing DBM of these small sizes, at least one stabilizing agent is used which retards the influx of host cells capable of removing such small particles (e.g., macrophages and foreign body giant cells) long enough to allow the active factors within the DBM to elicit an osteoinductive response. In addition or alternatively, a diffusion barrier will be present to retard the efflux of factors from the particles. In certain embodiments, the particles are at least 200 microns across the greatest dimension. The particles may be any shape including ovals, spherical, cuboidal, cones, pyramids, wedges, etc. In certain embodiments, the particles are wedges, pyramids, or cones being 200 microns across their largest dimension. In other embodiments, the DBM composition may include a mixture of several different sizes and/or shapes of particles.

Following particulation, the DBM is treated to remove mineral from the bone. While hydrochloric acid is the industry-recognized demineralization agent of choice, the literature contains numerous reports of methods for preparing DBM (see, for example, Russell et al. *Orthopaedics* 22(5):524–531, May 1999; incorporated herein by reference). For the purposes of the present invention, any material that provides a scaffolding containing active osteoinductive factors is considered DBM. The DBM may be prepared by methods known in the art or by other methods that can be developed by those of ordinary skill in the art without undue experimentation. In some instances, large fragments or even whole bone may be demineralized, and then particulated following demineralization. DBM prepared in this way is within the scope of the invention.

In the preparing the improved DBM compositions, the DBM component may be ground or otherwise processed into particles of an appropriate size before or after demineralization. In certain embodiments, the particle size is greater than 75 microns, more preferably ranging from about 100 to about 3000 microns, and most preferably from about 200 to about 2000 microns. After grinding the DBM component to the desired size, the mixture may be sieved to select those particles of a desired size. In certain embodiments, the DBM particles may be sieved though a 50 micron sieve, more preferably a 75 micron sieve, and most preferably a 100 micron sieve.

One particularly useful way to protect small size particles from cellular ingestion and/or provide a diffusion barrier is to embed them in a monolithic bioabsorbable matrix, and then fragment the particle-containing monolithic matrix into particle sizes greater than 70 microns, preferably greater than 100 microns, and most preferably greater than 150 microns in their smallest dimension. Preferred matrices for embedding small DBM particles include biocompatible polymers and setting calcium phosphate cements. Generally the particulate DBM/polymer weight ratio will range from about 1:5 to about 1:3. In the case of calcium phosphate, the DBM will be present up to 75% by weight. Particulation of the monolith can be accomplished by conventional milling or grinding, or through the use of cryomilling, or freezing followed by pulverization. In one preferred embodiment, lyophilized DBM is embedded in a resorbable polymer. In a second preferred embodiment, lyophilized DBM is embedded in one of the setting calcium phosphates known to the art.

Stabilizing Agents

Diffusion barriers. Diffusion barriers retard the diffusion of degradative enzymes and/or water to the active moieties within the inventive formulations. Enzymes retarded in their diffusion to the included DBM may be capable of releasing the active factor from the matrix, and/or degrading or inactivating the active factor. They also may act by retarding diffusion of the active factors from the implant site. In these ways, the barriers provide for longer residence time of the active factors at the implant site. This is particularly useful for forming bone in higher species such as humans, where bone formation appears to require the presence of active factors for longer times.

Generally, materials most suitable to serve as diffusion barriers will be easily mixed with DBM or synthetic matrix of choice to form a gel, paste, or putty-like consistency, although in some embodiments, the barrier/matrix formulation will be prepared as a relatively non-deformable solid (e.g., for matrix preparations to be used in posterior lateral spine fusion). In preferred embodiments, the diffusion barriers themselves degrade in a predictable manner to unmask active factors at a time later than would normally occur in the absence of a diffusion barrier. Resorbable polymers with known hydrolytic rates are useful as diffusion barriers as well as enzymatically degraded polymers. Particularly useful are lipase susceptible lipid based carriers such as fatty acids and phospholipids, which mix well with DBM. In certain DBM embodiments, the composition does not include phosphatidylcholine. Some particularly effective preparations provide prolonged stability by controlled unmasking of the osteoinductive factors. These preparations generally involve the use of two or more diffusion barriers with different degradation times affording at least two different rates of unmasking the same active factor.

Biodegradable polymers useful in preparing inventive stabilized matrix/growth factor compositions include natural polymers such as proteins (e.g., collagen) and polysaccharides (e.g., starch, modified starch, maltrin) as well as man-made resorbable polymers such as poly-orthoesters. These polymers when mixed with the inventive growth factor containing compositions retard diffusion of the host's degradative enzymes and/or water to the active factors contained within the composition, thereby retarding release and/or degrading of the active factor contained therein.

Polymers that may be included within inventive compositions include, for example, natural polymers such as lipids, polysaccharides, proteoglycans, and proteins. Preferred polysaccharides include starches, dextrans, and celluloses, and preferred proteins include collagen. Polysaccharides such as starches, dextrans, and celluloses may be unmodified or may be modified physically or chemically to affect one or more of their properties such as their characteristics in the hydrated state, their solubility, their susceptibility to degradation, or their half-life in vivo. Polysaccharides such as starches and celluloses are attractive as they also have known degradation rates. Generally, the celluloses degrade more slowly within the body, breaking down on the order of weeks or months, while many starch and lipid preparations degrade rapidly, on the order of hours or days. Starch in the natural state is a mixture of two polysaccharides, amylose and amylopectin. The susceptibility of the particular starch to the starch-degrading enzymes such as amylase, pectinases, and β-glucosidase is an important consideration in designing the inventive formulations. Those skilled in the art are aware of the variety of amylase susceptibilities of starches prepared from various plant sources and may apply this knowledge to produce formulations having a desired stability time. Preferred starches will degrade as much as 10% per day, preferably 50% per day, and most preferably greater than 90% per day. Those starches less susceptible to degradation by pectinase and/or amylase (amylase-resistant starch; Starch Australasia, Sydney, Australia) may be used to maximally extend the osteoinductive half-life in vivo to an even greater extent than improved DBM or synthetic growth factor/matrix formulations prepared from more enzyme susceptible starches. Some modified starches are less susceptible to degradation by amylase; therefore, improved DBM with modified starch would presumably have a longer half-life in vivo as compared to those improved DBM with unmodified starch. One preferred method to affect amylase susceptibility of starch is through the use of starch lipid combinations. Guidance for the combination of lipid and starch to affect amylase susceptibility is given by Crowe et al "Inhibition of Enzymic Digestion of Amylose by Free Fatty Acids In Vitro Contributes to Resistant Starch Formation" *J. Nutr.* 130(8):2006–2008, August 2000; incorporated herein by reference. Similar considerations apply to lipids and their degradative enzymes the lipases. A large variety of mono-, di-, and triglycerides with varying degrees of susceptibility to lipase degradation are available from commercial sources. Some embodiments include one or more polymeric materials, preferably biodegradable, such as tyrosine polycarbonates, polyfumarates, tyrosine polyarylates, and poly-orthoesters such as polylactide, polygalactide, and co-polymers thereof. These polymers are biodegradable, and their properties can be modified by altering the chain length or degree of cross-linking of the polymer and/or the chemical structure of the monomers. Additionally, co-polymers can be prepared using combinations of resorbable polymers.

Enzyme inhibitors. Alternatively or additionally, the inventive compositions may be stabilized by the addition of one or more degradation inhibitors, active against growth factor activity degrading agents found in the host organism and/or in the implant composition. These inhibitors may also inhibit the activity of enzymes responsible activating osteoinductive factors of the DBM composition. Degradation or activation inhibitors useful in the practice of the present invention may include, for example, acid protease inhibitors, serine protease inhibitors, metalloprotease inhibitors (shown in FIG. 6; also, see Whittaker et al. "Matrix Metalloproteinases and their Inhibitors-Current Status and Future Challenges" *Celltransmissions* 17(1):3–14; incorporated herein by reference), cysteine protease inhibitors, glyconase inhibitors, and glycosidase inhibitors. Specific protease inhibitors useful in the practice of the present invention include, for example, aprotinin, 4-(2-aminoethyl) benzenesulfonyl fluoride (AEBSF), amastatin-HCl, alpha1-antichymotrypsin, antithrombin III, alpha1-antitrypsin, 4-aminophenylmethane sulfonyl-fluoride (APMSF), arphamenine A, arphamenine B, E-64, bestatin, CA-074, CA-074-Me, calpain inhibitor I, calpain inhibitor II, cathepsin inhibitor, chymostatin, diisopropylfluorophosphate (DFP), dipeptidylpeptidase IV inhibitor, diprotin A, E-64c, E-64d, E-64, ebelactone A, ebelactone B, EGTA, elastatinal, foroxymithine, hirudin, leuhistin, leupeptin, alpha2-macroglobulin, phenylmethylsulfonyl fluoride (PMSF), pepstatin A, phebestin, 1,10-phenanthroline, phosphoramidon, chymostatin, benzamidine HCl, antipain, epsilon-aminocaproic acid, N-ethylmaleimide, trypsin inhibitor, 1-chloro-3-tosylamido-7-amino-2-heptanone (TLCK), 1-chloro-3-tosylamido-4-phenyl-2-butanone (TPCK), trypsin inhibitor, sodium EDTA, and the TIMPs class of metalloproteinase inhibitors. Particularly useful ones are those stable under acidic conditions and effective at acidic conditions. As will be appreciated by those of skill in this art, the less osteoinductive factors lost or degraded during the processing of the bone to form DBM the more will be available for recruitment once the DBM composition is implanted.

Competitive substrates. Use of competitive substrates for the host's degradative or activating enzymes may also be employed to stabilize the osteoinductive factors of the DBM or exogenously added growth factors. Examples of competitive substrates include di- and poly-lysines. Di- and polysaccharides can be employed as competitive substrates of glycosidases, amylases, and/or pectinases. Particularly useful are stereoisomers of the competitive substrates.

Masking entities. Specific masking entities are generally used to specifically block a single entity or class of entities from enzymatic breakdown. The degradative or activating enzyme to be blocked may be endogenous or exogenous to the matrix. The masking entities generally bind to a ligand present on the matrix which may or may not be the active factor itself. Once bound the masking entity sterically hinders the breakdown and/or release of one or more active factors. Over time the masking entity either unbinds or itself is degraded leaving the ligand and or growth factor susceptible to degradation. Diffusion barriers represent a generalized form of masking entity by preventing access of the degradative or activating enzymes to many or all the growth factors associated with the matrix.

Growth factor binding proteins: Virtually every extracellular matrix growth factor is know to be associated with a binding protein which regulates the activity of the growth factor. Purified preparations of these binding proteins can be prepared, and added to DBM preparations to serve as masking entitites. Typical growth factor binding proteins include but are not limited to noggin, chordin, follistatin, TGF-β binding protein, and insulin-like growth factor binding proteins. Agents may also be added to the DBM composition to induce the release of the growth factor from its binding protein. In certain embodiments, the agent known to induce release of the growth factor may be encapsulated in a biodegradable polymer so that the agent is released over an extended period of time, thereby leading to the release of growth factor over an extended period of time.

Lectins. Lectins are proteins which can bind to the sugar moieties of glycoproteins. Since growth factors are generally glycoproteins, lectins can be employed to bind to the growth factors and potentially retard or inhibit access of proteases or growth factor releasing enzymes to the active growth factors. Ideally the lectin will be selected according to the identity of the terminal sugar on the active glycoprotein of interest. Lectins include, but are not limited to, membrane-bound lectins, I-type lectins, and P-type lectins. Specific lectins include galectins, calcium-dependent lectins, selecting, collecting, and annexins.

Antibodies. Monoclonal or polyclonal antibodies specific to the active factors, or to those proteins known to bind to the active factors (see above) may be added to the inventive formulations to protect specific growth factors from degradative or releasing enzymes.

Inventive DBM compositions may alternatively or additionally be stabilized through exposure to conditions (e.g., pH, temperature, etc.) under which degrading agents do not function optimally or the degradatory enzymes will not function effectively (e.g., low pH).

Addition of enzyme inhibitors, competitive substrates, and masking agents. The incorporation of any of these entities into the inventive formulations, is generally accomplished by suspending the molecule or molecules of interest in an appropriately compatible buffer as will be known to those skilled in the art. This buffer will be mixed with lyophilized matrix in a relatively low liquid-to-solid volume ratio to form a slurry. The slurry is then lyophilized and used to prepare the desired DBM formulations.

One unexpected feature of the instant invention is that the incorporation of any of the inventive enzyme inhibitors, competitive substrates, or masking agents often has the additional feature of improving the DBM formulation shelf-life by preventing access of endogenously present degradative enzymes to the active factors present in the matrix. This is particularly true for DBM formulations which are prepared containing water (e.g., DBM preparations with hydrogel carriers such as hyaluronic acid or collagen, or hydrated starch carriers).

Many of the osteoinductive factors found in DBM are in cryptic form and must be "activated" or "released" in order to be osteoinductive. The activation of osteoinductive factors may involve a conformational change, a post-translational modification, a cleavage of the peptide, a change in tertiary or quaternary structure, release from the DBM, release from a binding protein, etc. For example, the factors may be in a pre- or pro-form which requires proteolytic cleavage to be active. In addition, the osteoinductive factors may be associated with a binding protein or a protein of the matrix of the DBM. The same processes such as proteolysis involved in degradation of the active factors may also be involved in the activation of these factors. Therefore, all the same methods described above that can be used to slow degradation may also affect activation rates. One of skill in the art preparing a DBM composition could balance the rates of degradation and activation to achieve a desired level of osteoinductivity from the implant over time. In addition, such factors as pH, ion concentration, or other factors which affect protein function and/or folding may affect the activation of osteoinductive factors found in DBM. These factors also may effect the release of a factor from its binding protein. In certain embodiments, for example, where pH plays a role in the activation of a factor, the DBM composition may include a chemical compound such as a polymer which will break down over time and release an acid by-product; thereby, activating the factors within the DBM composition. In other embodiments, a biodegradable polymer may release ions or a protease that is able to "activate" the osteoinductive factors of the DBM composition.

Release of the osteoinductive factors from the delivery matrix may also be important in its osteoinductivity. Many factors may be found bound to the DBM through specific binding proteins as described above or through non-specific interactions. A portion of the factors may need to be released from the matrix in order to be active while others may only be active while bound. For example, cells may be recruited to the matrix by certain factors, and then once there, the cells may interact with other factors bound to the matrix. The cells may need to interact with both the matrix and the factor to induce bone production. The rate of release of the osteoinductive factors may be controlled by diffusion barriers or agents which affect the binding of the factors to the matrix or their binding proteins. As described above, in certain embodiments, it is preferred that a diffusion barrier be degraded over time so as to release factors or allow recruited cells to interact with the matrix. Degradation of the diffusion barrier may also allow proteases into the DBM implant to activate and/or release osteoinductive factors.

As will be appreciated by one of skill in this art, the DBM composition may be prepared to balance degradation, activation, and release of osteoinductive factors to create a composition with a desired osteoinductive activity. The osteoinductivity of the DBM composition may be suited for a particular application, site of implant, or patient. For instance, certain application would require an extended period of osteoinductivity ranging from weeks to months; whereas other applications may only need osteoinductivity for days to weeks. One of skill in the art can prepare a DBM composition with a desired osteoinductivity time profile.

Test for Enhancement

The invention also provides a simple in vitro test for the screening of suitable stabilizing agents. DBM prepared with and without the biodegradable stabilizing agent is exposed under simulated physiological conditions (e.g., pH 7.4, physiological saline) to an enzyme or combination of enzymes known to be capable of degrading some or all of the protein constituents of the DBM. Most often this will be a protease such as trypsin, papain, peptidase, or the like. Evidence for matrix or matrix component breakdown is compared between the two preparations. Materials retarding the breakdown process are considered to be good candidates for further testing. Preferred indicators of breakdown include immunological detection of TGF-$\beta$ and/or IGF breakdown. In addition to the enzymes indicated above, other enzymes such as collagenases or combinations of enzymes as well as glycosidases may also be used. Particularly useful in this regard is the natural degradatory activity of serum or tissue extracts. Under these conditions, specific marker proteins present in the DBM may be tracked by immunological methods such as radioimmunoassay or gel electrophoresis utilizing western blots, or other analytical methods known in the art.

Following the identification of candidate stabilizers in the above assay, the DBM formulations containing the candidate stabilizers are tested in the osteoinductivity assays described elsewhere herein.

Osteoinducer

To the improved DBM may be added other osteoinducing agents. These agents may be added in an activated or non-activated form. These agents may be added at anytime during the preparation of the inventive material. For example, the osteoinducing agent may be added after the demineralization step and prior to the addition of the stabilizing agents so that the added osteoinducing agent is protected from exogenous degrading enzymes once implanted. In some embodiments the DBM is lyophilized in a solution containing the osteoinducing agent. In certain other preferred embodiments, the osteoinducing agents are adhered onto the hydrated demineralized bone matrix and are not freely soluble. In other instances, the osteoinducing agent is added to the improved DBM after addition of the stabilizing agent so that the osteoinducing agent is available immediately upon implantation of the DBM.

Osteoinducing agents include any agent that leads to or enhances the formation of bone. The osteoinducing agent may do this in any manner, for example, the agent may lead to the recruitment of cells responsible for bone formation, the agent may lead to the secretion of matrix which may subsequently undergo mineralization, the agent may lead to the decreased resorption of bone, etc. Particularly preferred osteoinducing agents include bone morphogenic proteins (BMPs), transforming growth factor (TGF-$\beta$), insulin-like growth factor (IGF-1), parathyroid hormone (PTH), and angiogenic factors such as VEGF. In one preferred embodiment (Example 12), the inducing agent is genetically engineered to comprise an amino acid sequence which promotes the binding of the inducing agent to the DBM or the carrier. Sebald et al. in PCT/EP00/00637, incorporated herein by reference, describe the production of exemplary engineered growth factors, suitable for use with DBM.

Formulation

Improved osteogenic compositions of the present invention may be formulated for a particular use. The formulation may be used to alter the physical, biological, or chemical properties of a DBM preparation. A physician would readily be able to determine the formulation needed for a particular application taking into account such factors as the type of injury, the site of injury, the patient's health, the risk of infection, etc.

Inventive compositions therefore may be prepared to have selected resorption/loss of osteoinductivity rates, or even to have different rates in different portions of an implant. For example, the formulation process may include the selection of DBM particles of a particular size or composition, combined with the selection of a particular stabilizing agent or agents, and the amounts of such agents. To give but one example, it may be desirable to provide a composition whose osteoinductive factors are active in a relatively constant amount over a given period of time. A DBM composition comprising factors with longer half-lives can be prepared using a less biodegradable polymer or a larger amount (e.g., a thicker coating) of polymeric compound. Alternatively or additionally, the particle size may be important in determining the half-life of the inventive DBM composition. In certain preferred embodiments, an inventive formulation may include a mixture of particles, each with a different half-life. Such a mixture could provide the steady or possible unmasking of osteoinductive factors over an extended period of time ranging from days to weeks to months depending on the needs of the injury. Compositions such as this one can be formulated to stimulate bone growth in a human patient comparable to the bone growth induced by treatment with 10 µg of rhBMP on a collagen sponge, and preferably comparable to 100 µg, and most preferably 1–10 mg rhBMP.

Physical properties such as deformability and viscosity of the DBM may also be chosen depending on the particular clinical application. The particles of the improved DBM may be mixed with other materials and factors to improve other characteristics of the implant. For example, the improved DBM material may be mixed with other agents to improve wound healing. These agents may include drugs, proteins, peptides, polynucleotides, solvents, chemical compounds, biological molecules.

The particles of DBM (or inventive DBM material) may also be formed into various shapes and configurations. The particles can be formed into rods, strings, sheets, weaves, solids, cones, discs, fibers, wedges etc. In certain embodiments, the shape and size of the particles in the DBM composition affect the time course of osteoinductivity. For example, in a cone or wedge shape, the tapered end will result in osteoinductivity shortly after implantation of the DBM composition, whereas the thicker end will lead to osteoinductivity later in the healing process (e.g., hours to days to weeks later). In certain embodiments, the particle have a length of greater than 2 mm, greater than 1.5 mm, greater than 1 mm, preferably greater than 500 microns, and most preferably greater than 200 microns across its widest dimension. Also, larger particle size will have induce bone formation over a longer time course than smaller particles. Particles of different characteristics (e.g., composition, size, shape) may be used in the formation of these different shapes and configurations. For example, in a sheet of DBM a layer of long half-life particles may be alternated between layers of shorter half-life particles (See U.S. Pat. No. 5,899,939, incorporated herein by reference). In a weave, strands composed of short half-life particles may be woven together with strands of longer half-lives.

In one preferred embodiment of the invention, fibrous DBM is shaped into a matrix form as described in U.S. Pat. No. 5,507,813, incorporated herein by reference, and Examples 13 & 14 (embedded matrix fabrication) below. The shaped DBM is then embedded within a diffusion barrier type matrix, such that a portion of the matrix is left exposed free of the matrix material. Particularly preferred blocking matrices are starch, phosphatidyl choline, tyrosine polycarbonates, tyrosine polyarylates, polylactides, polygalactides, or other resorbable polymers or copolymers. Devices prepared in this way from these matrices have a combination of immediate and longer lasting osteoinductive properties and are particularly useful in promoting bone mass formation in human posterolateral spine fusion indications.

In another embodiment of the invention, inventive DBM compositions having a pre-selected three-dimensional shape are prepared by repeated application of individual layers of DBM, for example by 3-D printing as described by Cima et al. U.S. Pat. Nos. 5,490,962; and 5,518,680, each of which is incorporated herein by reference; and Sachs et al. U.S. Pat. No. 5,807,437, incorporated herein by reference. Different layers may comprise individual stabilized DBM preparations, or alternatively may comprise DBM layers treated with stabilizing agents after deposition of multiple layers.

In the process of preparing improved inventive DBM materials, the materials may be produced entirely aseptically or be sterilized to eliminate any infectious agents such as HIV, hepatitis B, or hepatitis C. The sterilization may be accomplished using antibiotics, irradiation, chemical sterilization (e.g., ethylene oxide), or thermal sterilization. Other methods known in the art of preparing DBM such as defatting, sonication, and lyophilization may also be used in preparing the improved DBM. Since the biological activity of demineralized bone is known to be detrimentally affected by most terminal sterilization processes, care must be taken when sterilizing the inventive compositions. In preferred embodiments, the DBM compositions described herein will be prepared aseptically or sterilized as described in Example 11.

Applications

Improved osteogenic compositions of the present invention may be used to promote the healing of bone injuries. The compositions may be used in any bone of the body on any type of injury. The improved DBM composition has been designed to produce bone in human patients with similar timing and at a level similar to 10 µg to 100 µg, preferably 200 µg to 1 mg of rhBMP on a collagen sponge. For example, specific bones that can be repaired using the inventive material include the ethmoid, frontal, nasal, occipital, parietal, temporal, mandible, maxilla, zygomatic, incus, stapes, malleus, cervical vertebrae, thoracic vertebrae, lumbar vertebrae, sacrum, sternum, ribs, clavicle, scapula, humerus, ulna, radius, carpal bones, metacarpal bones, phalanges, ileum, ischium, pubis, pelvis, femur, patella, tibia, fibula, calcaneus, talus, and metatarsal bones. The type of injury amenable to treatment with the improved DBM include bone defects resulting from injury, brought about during the course of surgery, infection, malignancy, or developmental malformation. The inventive material may be useful in orthopaedic, neurosurgical, cosmetic, and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery (e.g., deficit filling), discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, etc.

Inventive DBM compositions may also be used as drug delivery devices. In certain preferred embodiments, association with the inventive DBM composition increases the half-life of the relevant biologically active agent(s). Particularly preferred inventive drug delivery devices are used to deliver osteoinductive growth factors. Other preferred agents to be delivered include factors or agents that promote wound healing. However, inventive compositions may alternatively or additionally be used to deliver other pharmaceutical agents including antibiotics, anti-neoplastic agents, growth factors, hematopoietic factors, nutrients, etc. Bioactive agents that can be delivered using the inventive DBM composition include non-collagenous proteins such as osteopontin, osteonectin, bone sialo proteins, fibronectin, laminin, fibrinogen, vitronectin, trombospondin, proteoglycans, decorin, proteoglycans, beta-glycan, biglycan, aggrecan, veriscan, tenascin, matrix gla protein hyaluronan; cells; amino acids; peptides; inorganic elements; inorganic compounds; organometallic compounds; cofactors for protein synthesis; cofactors for enzymes; vitamins; hormones; soluble and insoluble components of the immune system; soluble and insoluble receptors including truncated forms; soluble, insoluble, and cell surface bound ligands including truncated forms; chemokines, interleukins; antigens; bioactive compounds that are endocytosed; tissue or tissue fragments; endocrine tissue; enzymes such as collagenase, peptidases, oxidases, etc.; polymeric cell scaffolds with parenchymal cells; angiogenic drugs, polymeric carriers containing bioactive agents; encapsulated bioactive agents; bioactive agents in time-release form; collagen lattices; antigenic agents; cytoskeletal agents; cartilage fragments; living cells such as chondrocytes, osteoblasts, osteoclasts, fibroblasts, bone marrow cells, mesenchymal stem cells, etc.; tissue transplants; bioadhesives; bone morphogenic proteins (BMPs), transforming growth factor (TGF-beta), insulin-like growth factor (IGF-1, IGF-2), platelet derived growth factor (PDGF); fibroblast growth factors (FGF), vascular endothelial growth factor (VEGF), epidermal growth factor (EGF), growth factor binding proteins, e.g., insulin-like growth factor binding protein (IGFBP-2, IGFBP-3, IGFBP-4, IGFBP-5, IGFBP-6); angiogenic agents; bone promoters; cytokines; interleukins; genetic material; genes encoding bone promoting action; cells containing genes encoding bone promoting action; cells genetically altered by the hand of man; externally expanded autograft or xenograft cells; growth hormones such as somatotropin; bone digestors; antitumor agents; fibronectin; cellular attractants and attachment agents; immunosuppressants; bone resorption inhibitors and stimulators; mitogenic factors; bioactive factors that inhibit and stimulate second messenger molecules; cell adhesion molecules, e.g., cell-matrix and cell-cell adhesion molecules; secondary messengers; monoclonal antibodies specific to cell surface determinants on mesenchymal stem cells; portions of monoclonal antibodies specific to cell surface determinants on mesenchymal stem cells; clotting factors; polynucleotides; and combinations thereof. The amount of the bioactive agent included with the DBM composition can vary widely and will depend on such factors as the agent being delivered, the site of administration, the patient's physiological condition, etc. The optimum levels being determined in a specific case based upon the intended use of the implant.

For example, inventive DBM compositions may be prepared so that they include one or more compounds selected from the group consisting of drugs that act at synaptic and neuroeffector junctional sites (e.g., acetylcholine, methacholine, pilocarpine, atropine, scopolamine, physostigmine, succinylcholine, epinephrine, norepinephrine, dopamine, dobutamine, isoproterenol, albuterol, propranolol, serotonin); drugs that act on the central nervous system (e.g., clonazepam, diazepam, lorazepam, benzocaine, bupivacaine, lidocaine, tetracaine, ropivacaine, amitriptyline, fluoxetine, paroxetine, valproic acid, carbamazepine, bromocriptine, morphine, fentanyl, naltrexone, naloxone,); drugs that modulate inflammatory responses (e.g., aspirin, indomethacin, ibuprofen, naproxen, steroids, cromolyn sodium, theophylline); drugs that affect renal and/or cardiovascular function (e.g., furosemide, thiazide, amiloride, spironolactone, captopril, enalapril, lisinopril, diltiazem, nifedipine, verapamil, digoxin, isordil, dobutamine, lidocaine, quinidine, adenosine, digitalis, mevastatin, lovastatin, simvastatin, mevalonate); drugs that affect gastrointestinal function (e.g., omeprazole, sucralfate); antibiotics (e.g., tetracycline, clindamycin, amphotericin B, quinine, methicillin, vancomycin, penicillin G, amoxicillin, gentamicin, erythromycin, ciprofloxacin, doxycycline, acyclovir, zidovudine (AZT), ddC, ddI, ribavirin, cefaclor, cephalexin, streptomycin, gentamicin, tobramycin, chloramphenicol, isoniazid, fluconazole, amantadine, interferon,); anti-cancer agents (e.g., cyclophosphamide, methotrexate, fluorouracil, cytarabine, mercaptopurine, vinblastine, vincristine, doxorubicin, bleomycin, mitomycin C, hydroxyurea, prednisone, tamoxifen, cisplatin, decarbazine); immunomodulatory agents (e.g., interleukins, interferons, GM-CSF, TNFα, TNFβ, cyclosporine, FK506, azathioprine, steroids); drugs acting on the blood and/or the blood-forming organs (e.g., interleukins, G-CSF, GM-CSF, erythropoietin, vitamins, iron, copper, vitamin $B_{12}$, folic acid, heparin, warfarin, coumarin); hormones (e.g., growth hormone (GH), prolactin, luteinizing hormone, TSH, ACTH, insulin, FSH, CG, somatostatin, estrogens, androgens, progesterone, gonadotropin-releasing hormone (GnRH), thyroxine, triiodothyronine); hormone antagonists; agents affecting calcification and bone turnover (e.g., calcium, phosphate, parathyroid hormone (PTH), vitamin D, bisphosphonates, calcitonin, fluoride), vitamins (e.g., riboflavin, nicotinic acid, pyridoxine, pantothenic acid, biotin, choline, inositol, carnitine, vitamin C, vitamin A, vitamin E, vitamin K), gene therapy agents (e.g., viral vectors, nucleic-acid-bearing liposomes, DNA-protein conjugates, anti-sense agents); or other agents such as targeting agents etc.

In certain embodiments, the agent to be delivered is adsorbed to or otherwise associated with the matrix being implanted. The agent may be associated with the matrix of the DBM composition through specific or non-specific interactions; or covalent or non-covalent interactions. Examples of specific interactions include those between a ligand and a receptor, a epitope and an antibody, etc. Examples of non-specific interactions include hydrophobic interactions, electrostatic interactions, magnetic interactions, dipole interactions, van der Waals interactions, hydrogen bonding, etc. In certain embodiments, the agent is attached to the matrix using a linker so that the agent is free to associate with its receptor or site of action in vivo. In certain preferred embodiments, the agent to be delivered may be attached to a chemical compound such as a peptide that is recognized by the matrix of the DBM composition. In another embodiment, the agent to be delivered is attached to an antibody, or fragment thereof, that recognizes an epitope found within the matrix of the DBM composition. In a particularly preferred embodiment, the agent is a BMP, TGF-β, IGF, parathyroid hormone (PTH), growth factors, or angiogenic factors. In certain embodiments at least two bioactive agents are attached to the DBM composition. In other embodiments at least three bioactive agents are attached to the DBM composition.

The growth factor stabilizing strategies described herein, may also be applied directly to growth factors associated with synthetic matrices such as ceramics, bone cements, or polymers. In these embodiments one, two, or more growth factors are associated with the synthetic matrix. A growth factor is associated with an anchoring matrix (e.g., amorphous or crystalline calcium phosphate associated with a growth factor such as BMP), wherein the composition is prepared in the presence of a diffusion barrier such as amylose, fatty acid, or a resorbable polymer, or with a combination of at least two or more of these stabilizing agents. In a preferred embodiment, a poorly crystalline calcium phosphate is associated with a growth growth factor mixed with a starch/lecithin diffusion barrier.

These and other aspects of the present invention will be further appreciated upon consideration of the following Examples, which are intended to illustrate certain particular embodiments of the invention but are not intended to limit its scope, as defined by the claims.

EXAMPLES

Example 1

Preparing Demineralized Bone Matrix (DBM)

DBM may be prepared using any method or technique known in the art (see Russell et al. *Orthopedics* 22(5): 524–531, May 1999; incorporated herein by reference). The following is an exemplary procedure for preparing demineralized bone derived from Glowacki et al. "Demineralized Bone Implants" *Clinics in Plastic Surgery* 12(2):233–241, April 1985, which is incorporated herein by reference. Bones or bone fragments from donors are cleaned to remove any adherent periosteum, muscle, connective tissue, tendons, ligaments, and cartilage. Cancellous bone may be separated from dense cortical bone and processed as large pieces. Cortical bone may be cut into small pieces to improve the efficiency of subsequent washes and extractions. Denser bone from larger animals may need to be frozen and hammered in order to produce chips less than 1 cm. The resulting pieces of bone are thoroughly washed with cold, deionized water to remove marrow and soft tissue.

The cleaned bone is then extracted with frequent changes of absolute ethanol for at least 1 hour. Typically, a total of 4 liters of ethanol is used per 100 g of bone. The bone is then extracted with frequent changes of anhydrous diethyl ether in a fume hood for 1 hour. Typically, 2 liters of ether is used per 100 g of bone. The bone is dehydrated by these extractions of ethanol and ether and can be stored at room temperature.

The dehydrated bone is then frozen and then pulverized in a liquid nitrogen impacting mill. Pulverized bone is then sieved into fractions of 75 to 250, 250 to 450, and greater than 450 microns. Bone particle fractions are then demineralized using 0.5 M hydrochloric acid (50 ml per gram) for 3 hours at room temperature or at 4° C. on magnetic stirrers with insulation to prevent overheating. Large chips of bone and blocks are extracted completely at 4° C. with frequent changes of 0.5 M hydrochloric acid. The demineralization process can be monitored radiographically, by ashing, or by nondecalcified histologic techniques (von Kossa stain). The acid and liberated minerals are washed away with cold, deionized water until the pH of the wash matches the pH of the water. The water washes can be decanted from the large particles and chips of bone; however, the washes must be removed by centrifugation from the finer particles. The washing step requires approximately 500 ml of water per gram of starting bone particles.

Demineralized bone powders are extracted with changes of absolute ethanol for 1 hour using 200 ml of ethanol per gram of starting bone particles. The material is extracted in a fume hood with changes of anhydrous ethyl ether for 1 hour with 100 ml of ether per gram of starting bone particles. After the last change of ether is removed, the demineralized bone powder is left overnight in the hood until all the residual ether has vaporized. The particles should be odorless, snow-white, and discrete. To sterilize the demineralized bone material, it may be treated with cold ethylene oxide or irradiated.

To test the bioactivity of the prepared DBM, 25 mg of the material is implanted into each of two thoracic subcutaneous pockets in shaved, anesthetized 28-day old male Charles River CD rats. The implanted specimens may then be harvested and inspected several days after implantation. The composition of the induced tissue can be quantified by histomorphometric analysis and be biochemical techniques.

Example 2

Another Method of Preparing DBM.

DBM may be prepared using any method or techniques known in the art (See Russell et al. *Orthopedics* 22(5): 524–53 1, May 1999; incorporated herein by reference).

Demineralized bone matrix was prepared from long bones. The diaphyseal region was cleaned of any adhering soft tissue and then ground in a mill. Ground material was sieved to yield a powder with particles approximately 100 μm to 500 μm in diameter. The particulate bone was demineralized to less than about 1% (by weight) residual calcium using a solution of Triton X-100 (Sigma Chemical Company, St. Louis, Mo.) and 0.6N HCl at room temperature followed by a solution of fresh 0.6N HCl. The powder material was rinsed with deionized water until the pH was greater than 4.0. It then was soaked in 70% ethanol and freeze-dried to less than 5% residual moisture.

Example 3

Formulating Preferred Inventive DBM Compositions

The carrier was prepared by mixing approximately 6.5% (w/w) of the modified starch, B980, with approximately 30% (w/w) maltodextrin (M180) and approximately 63.5% (w/w) sterile, deionized water. The mixture was heated to 70° C. to pre-gelatinize. The pre-gelatinized mixture was then transferred into a steam autoclave and sterilized/gelatinized at 124° C. for 2 hours. The resulting mixture then had a consistency of pudding. The cooled carrier mixture was then combined with DBM (from Example 2) and water, in a ratio of approximately 27:14:9, respectively. The stabilized DBM was then implanted into athymic rats to assess osteoinductivity.

Alternative embodiments: Other components such as glycerol were added as a solution (approximately 20% w/v) in water instead of water at the time of pre-gelatinization or during the final composition mixing and were found to have acceptable handling characteristics.

Example 4

Stabilized DBM

The table below describes the preparation of a variety of inventive DBM compositions with different stabilizers. All preparations are prepared aseptically, and all preparations may be used with DBM particles, fibers, or solid formed matrices.

Example 5

In Vitro Assessment of Protective Agents

Samples of DBM with carrier with, and without stabilizing agents (or various concentrations and/or formulations of stabilizing agents) are prepared and incubated with serum or individual enzymes (e.g., papain) in pH 7.4 PBS buffer and incubated at 37° C. for 0.5, 1, 2, 4, 8, and 24 hours Samples are then extracted to determine the concentrations of growth factors and other matrix proteins as outlined in Ueland et. al. ("Increased cortical bone content of insulin-like growth factors in acromegalic patients" *J Clin Endocrinol Metab* 1999 January;84(1):123–7; incorporated herein by reference). Samples are prepared for native and denaturing SDS gel electrophoresis followed by Western blot analysis or Western Ligand blotting as described in Ueland et al. (1999) and incorporated herein by reference (Ueland et al "Increased cortical bone content of insulin-like growth factors in acromegalic patients" *J Clin Endocrinol Metab* 1999 January;84(1):123–7; and Walker, J. M. (Ed) *The Protein Protocols Handbook*, Second Edition 2002, Humana Press Totowa, N.J.; each of which is incorporated herein by reference).

Samples containing stabilizing agents demonstrating less degradation of growth factors or other proteins than samples without stabilizing agents are then tested for osteoinductivity at 7, 14, 21, and 28 days in the athymic rat assay. Extract samples can also be tested rapidly for biological activity in a tissue culture assay as described in Zhang et al. (1997).

| Class of Stabilizer | Stabilizer | DBM form | Method |
|---|---|---|---|
| Diffusion Barrier | Resorbable polymers in powdered form: Tyrosine poly arylate Tyrosine polycarbonate polyorthoester | Approximately 150–1000 micron particles lyophilized and then pre-swollen with 100% glycerol, excess removed by filtration | Pre-swollen particles are mixed with polymer powder. The mixture is Melt cast at 60–115° C. Following cooling the polymer DBM monolith is pulverized |
| | Phosphatidyl choline Phosphatidyl-ethanolamine Squalene Starch phosphatidyl choline | Approximately 150–1000 micron particles lyohillized | One or more of the indicated lipids are blended with the DBM to prepare a paste containing about 30–80% DBM |
| Masking Agent Lectins Antibodies Human Anti-noggin Human Anti-BMP Factor binding proteins Noggin Chordin TGBP Enzyme Inhibitors TIMPs Soybean trypsin Competitive Substrates Poly-lys-arg Di-mannose Poly-mannose Poly-L-lysine | Suspend in standard buffer system for the specific protein or PBS, or 1 mMHCl to a concentration ranging from about 1 ng/ml to about 10 mg/ml | Mix lyophilized DBM with protein solution to prepare a thick slurry (~0.33 gm/mL). Re-lyophilize. | Apply DBM particles as usual or mix with standard DBM carrier (e.g., glycerol, starch, pluronic) prior to application. |

Example 6

Determining Time Course for Induction of Bone Growth by Intermuscular Implant This Example characterizes the time course of induction of bone growth in an intermuscular site using the inventive materials, as compared with DBM base powder (as in Example 1), at time points of 7, 14, 28, and 35 days. This Example is similar to the rat model for assessing osteoinduction of DBM found in Edwards et al "Osteoinduction of Human Demineralized Bone: Characterization in a Rat Model" *Clinical Orthopaedics* 357:219–228, December 1998; incorporated herein by reference.

The study was conducted in athymic (nude) rats in order to minimize the potential for a cross-species incompatibility response to human tissue implants. The hind-limb intermuscular site was used for the initial determination of heterotopic bone induction properties because the site does not naturally contain bone.

Female homozygous mu/mu rats in the 50–75 g range were obtained from Harlan (Indianapolis, Ind.). The rats were housed for one week for acclimatization purposes prior to surgery. Sterile microisolator cages were used throughout the investigation, with sterile water and rodent diet provided ad libitum.

Implant Placement: A single intermuscular (IM) site was utilized in each hind limb of 30 rats. To provide a common positive control over all animals, a single 40 mg sample of rat DBM powder was placed intramuscularly within the left pectoralis (LP) muscle of each rat. Animals were allowed normal activities following surgical procedures.

Implant Materials: DBM and test materials were kept at room temperature. Eight 145 mg samples of Test and eight 40-mg samples of DBM powder were tested for implantation times of 7, 14, and 28 days. Six samples of each were tested at 35 days. The 40 mg samples of DBM powder were rehydrated with 100 μl of sterile ALLOPREP™ (Osteotech, Eatontown, N.J.). Each of the samples was packed into a 1 ml blunt cut syringe. Implantation was randomized so that a single animal did not receive two of the same implants.

Anesthesia: The rats were anesthetized with a mixture of ketamine (200 mg), xylazine (400 mg), and physiological saline (10 ml). The dosage was 3.5 ml/kg body weight administered intraperitoneally.

Procedure: Aseptic surgical procedures were carried out in a laminar airflow hood. A 1-cm skin incision was made on each upper hind limb using a lateral approach, and the skin was separated from the muscle by blunt dissection. A superficial incision aligned with the muscle plane was made to allow for insertion of the tips of the scissors. Blunt dissection was performed from this line deep into the muscle to create a pocket to hold the implanted material. A single suture was inserted to close the muscle pocket, and the skin was closed with metal clips.

Implantation of specimens in the left pectoralis muscles involved making a 1-cm skin incision over the chest, blunt dissection of the muscle to create a pocket, and positioning of the rat DBM powder using a blunt syringe. A single suture was inserted to close the muscle pocket, and the skin is closed with metal clips.

Rats were euthanized with $CO_2$ following the designated implantation time. Implant materials were located by palpitation, retrieved by blunt dissection, and cleaned of the surrounding tissue by careful trimming. An observer blinded to implant type performed a macroscopic evaluation of the implant material. Color, vascularity, hardness, and integrity were scored according to the scheme outlined in the Table below. (The highest score for the most robust response would be a 4 while a specimen showing little or no osteoinductive potential would score a 0.) Experience with this model has shown a high correlation between visual observations and histological observations of implant performance only at the extremes of both ends of the scale.

| Macroscopic Observation Scoring Guidelines | | | |
|---|---|---|---|
| Color: | White (W) | Grey (G) | Red (R) |
| Vascularity: | None (N) | Some (S) | Robust (R) |
| Hardness: | Mushy (M) | Firm (F) | Hard (H) |
| Integrity: | Diffuse (D) | Flat (F) | Nodule (N) |
| Score: | 0 | 0.5 | 1 |

Histology: Retrieved materials were fixed in Neutral buffered formalin. After fixation in formalin, samples were decalcified in 10% formic acid, dehydrated in graded alcohols, embedded in JB-4 (glycol methacrylate, Polysciences, Inc., Warrington, Pa.) and sectioned, Five-micron sections were stained with toluidine blue and evaluated by light microscopy.

The explants were histologically evaluated using a semi-quantitative method. Briefly, a numerical score based on a five-point scale was assigned to each section of nodule: 4=more then 75% involved in new bone formation; 3=51–75% involved in new bone formation; 2=26–50% involved in new bone formation; 1=1–25% of the explant involved in new bone formation; and 0=no evidence for the process of endochondral bone formation including the presence of cartilage or chondrocytes, active osteoblasts, osteoid, newly formed and mineralized bone, and/or marrow and associated fat cells.

| Scoring of Histological Sections | |
|---|---|
| Score | New Bone Formation |
| 0 | No new bone formation |
| 1 | <25% new bone formation |
| 2 | 26–50% new bone formation |
| 3 | 51–75% new bone formation |
| 4 | >75% new bone formation |

Following histological analysis, average scores were calculated for each material type. Based on previous experience with this animal model, each group was assigned an assessment of osteoinductive potential based on the average histological score.

Results: This protocol was followed with the test material, a DBM with a starch stabilizer as described in example 3, as compared with control GPS1-2 base DBM powder. At the 7-day timepoint, DBM with a starch stabilizer and GPS 1-2 powder achieved the same level of induction, with a histologic score of 0.9±0.4 and 1.0±0, respectively. All samples were hypercellular with a few chondrocytes present. At the 14-day timepoint, the DBM with a starch stabilizer achieved a greater level of induction than the GPS1-2 powder, with a histologic score of 3.6±0.5 and 2.9±1.0 respectively. Clusters of chondrocytes were present in all of the DBM with a starch stabilizer samples. At this time point, half of the powder samples also had clusters of chondrocytes, or scattered cells. At the 28-day point, few chondrocytes were present in either the DBM with a starch stabilizer or the GPS1-2 powder. Most samples exhibited mature bone by this stage. Some tissue infiltration was noted in three of the DBM with a starch stabilizer samples and two of the powder samples. The histologic score for the DBM with a starch stabilizer samples and two of the powder samples. The histologic score for the DBM with a starch stabilizer remained constant after the 14 days, whereas the histologic score for the powder improved from 2.9±1.0 to 3.9±0.4 between days 14 and 35 days, without significant change noted for those samples at the 35-day time point

| Product | Mean Histologic Scores | | | |
|---|---|---|---|---|
| | 7-Day | 14-Day | 28-Day | 35-Day |
| DBM (GPS1-2) with a starch stabilizer | 0.9 ± 0.4 | 3.6 ± 0.5 | 3.6 ± 0.5 | 3.5 ± 0.8 |
| DBM (GPS1-2) powder (Control) | 1.0 ± 0 | 2.9 ± 1.0 | 3.9 ± 0.4 | 3.7 ± 0.5 |

Conclusions: The results of this study indicated that the rate of induction for the DBM with a starch stabilizer increased to the 14-day timepoint and remained elevated through the end of the time course. The GPS 1-2 powder exhibited induction at a slower rate at the 14-day time point but was the same as the DBM with a starch stabilizer samples by 28 days. At this point, the osteoinductive potential for both products was nearly the same with only a difference of 0.3 in mean histologic scores and remained the same at the 35-day time point. The DBM with a starch stabilizer sample showed a faster rate of bone formation compared to the powder control. The qualitative evaluation of increased number of chondrocytes present was indicative of increased bone formation in the DBM with a starch stabilizer samples.

Example 7

Evaluating Efficacy of Inventive Compositions in Healing Bone Defects

Background Information: Morselized autogenous cancellous bone (ABG) has long been considered the "gold standard" for osteoinduction when a bone graft is required in an orthopedic clinical situation. Unfortunately, the amount of ABG available is limited, and there is at least a 5% surgical morbidity associated with the harvesting procedure. Demineralized bone matrix (DBM) has been shown to have equal to superior healing potential to ABG. One of the major disadvantages to demineralized bone matrix is that it often does not hold the three dimensional space of the defect. Thus, invasion of the defect site occurs from the surrounding muscle tissue. The test article, DBM with a starch stabilizer, offers a semi-solid texture so that the three dimensional space was maintained.

The rabbit ulna defect model has been modified and used in numerous projects to test the efficacy of osteoinductive and osteoconductive growth factors and matrices as substitute to autogenous bone graft. The aim of this study was to evaluate the bone inducing capacity of the new DBM formulation grafting material in comparison to previous formulations and ABG.

Materials and Methods:

Study Design Summary:

A. Rabbit bilateral 2-cm ulnar defects.

Treatment groups:
1. DBM+starch
2. Starch Carrier alone
3. Autograft (historical data used for comparison)

Surgical Procedure: Six months old male New Zealand white rabbits were used. A 2.0 centimeter non-uniting defect was surgically created in the bilateral ulnae of all rabbits. After complete periostectomy, thorough defect wash, and partial diaphyseal wash, grafting was implanted (according to test groups) via open surgical technique into each defect. The wound was closed primarily in layers. The test groups are listed in the table below. When anesthesia was achieved, both forelimbs were shaved and prepared with the rabbit supine (limbs up) position. Longitudinal incisions (3–4 cm) were made over both ulnae and the diaphysis (midshaft) portion of the ulna was exposed. The distal osteotomy was made 1 cm from the ulnocarpal (wrist) joint and the proximal osteotomy made 3.0 cm from the ulnocarpal joint, to create a 2 cm defect. The osteotomies were created with a high speed burr. The resultant loose block of diaphyseal bone was excised with its periosteum intact. Due to the very adherent interosseous membrane of the rabbit forelimb, internal fixation was not required. After irrigation with sterile saline to remove blood, bone, and marrow remnants, the implant material was placed in the defect. The deep fascial layer was closed as an envelope around the defect with 3–0 chromic suture. The skin was closed with interrupted nylon suture. A post-operative dressing/splint was applied and removed on the fourth post-operative day.

Radiographs: Antero-posterior radiographs were obtained immediately post-operatively and additional radiographs were taken at 3, 6, 9, and 12 weeks. High resolution (Faxitron) radiographs were taken of both limbs after excision and cleaned of soft tissue at either 6 or 12 weeks. Three blinded observers asses each time point for bone formation and remodeling.

Results: In vivo radiographs at 3 weeks indicated bone formation was evident in the starch-based formulation (FIG. 1). At 6 weeks, trabeculation was observed and almost complete bridging of the critical-sized defect with the starch-based formulation (FIG. 2).

Conclusion: The starch-based formulation appeared to improve the rate at which bone formation developed.

Example 8

The Following Table Summarizes the Results of Biocompatibility and Safety Studies for the Starch-Based Diffusion Barrier DBM Formulation of Example 3.

All studies listed in the table below, with the exception of study #12, were performed by NAMSA (North American Science Associates, Inc.)—ISO 9001 certified and fully accredited by the Association for Assessment and Accreditation of Laboratory Animal Care International (AAALAC). FDA guidelines were followed and NAMSA is registered with the USDA. All samples submitted to NAMSA were tested according to laboratory quality guidelines necessary to assure valid data.

| | Starch Diffusion Barrier DBM Formulation Testing MATERIAL ABSORBED WITHIN 30 DAYS | | | | |
|---|---|---|---|---|---|
| No. | TEST NAME | TEST MATERIAL | MODEL | METHOD | PASS/FAIL-COMMENTS |
| 1 | Cytotoxicity | Saline Extraction-Carrier (M180/B980) (4 g:20 ml extract) | In vitro assay - L-929 mouse fibroblasts | 48 hour read | Pass - Non-cytotoxic |
| 2 | Hemolysis | Saline Extraction-Carrier (M180/B980) (4 g:20 ml extract) | In vitro assay - rabbit blood | | Pass - Non hemolytic |
| 3 | Pyrogen | Saline Extraction-Carrier (M180/B980) (4 g:20 ml extract) | Intravenous injection - Rabbit | Repeated measures 1–3 hours post injection | Pass - Non-pyrogenic |
| 4 | Genotoxicity | a. Saline Extraction-Carrier (M180/B980) (4 g:20 ml extract) b. DMSO Extraction-Carrier (M180/B980) (4 g:20 ml extract) | In vitro - Ames Assay | Measurement of revertants | a. Pass - Non-mutagenic b. Pass - Non mutagenic |
| 5 | Acute Systemic Toxicity | a. Saline Extraction-Carrier (M180/B980) (4 g:20 ml extract) b. Cottonseed oil Extraction-Carrier (M180/B980) (4 g:20 ml extract) | Saline extract - IV injection - mice Cottonseed oil extraction - IP injection - mice | 4, 24, 48, 72 hour reads | a. Pass - Non toxic b. Pass - Non toxic |
| 6 | Sensitization | a. Saline Extraction-Carrier (M180/B980) (4 g:20 ml extract) b. Cottonseed oil Extraction-Carrier (M180/B980) (4 g:20 ml extract) Topical Application | Maximization Assay - Guinea pigs | Induction I (zero time) Induction II (6 days) Challenge (13 days post induction II) - 24, 48, 72 hour reads | Induction I: no abnormalities detected Induction I: no abnormalities detected Challenge: No evidence of causing delayed dermal contact sensitization |
| 7 | Intracutaneous Reactivity | a. Saline Extraction-Carrier (M180/B980) (4 g:20 ml extract) b. Cottonseed oil Extraction-Carrier (M180/B980) (4 g:20 ml extract) | 0.2 ml subcutaneous injection @ five separate sites of each of 3 rabbits | 24, 48, 72 hour reads | a. Pass - Non irritant b. Pass - Non-irritant |
| 8 | Muscle Implantation Study (Pilot) | a. Final product (rabbit specific) b. Carrier (M180/B980) | 6 × 2 ml portions over dorsolumbar region | 1, 2, 4 and 24 hour reads | Complies with clearance of <30 days Clearance in <1 week |
| 9 | Muscle Implantation Study - Histo-pathology | a. Final product (rabbit specific) b. Carrier (M180/B980) c. Rabbit DBM powder alone | Rabbit, Surgical Method 0.2 ml implanted | 3 and 7 days reads Irritation and toxicity evaluation | a. Pass - non-irritant b. Pass - non-irritant a. Pass - non-irritant |
| 10 | Implantation-Clearance Study | Final Formulation - Dog specific | Dog; Intramuscular Implantation To Absorption; Site Adjacent to Ribs; 30 cc volume. N = 3 | 3 time points: 2, 4, 6 weeks. Subsequent reads subject to bioresorption profile | Clearance <2 weeks |

-continued

Starch Diffusion Barrier DBM Formulation Testing MATERIAL ABSORBED WITHIN 30 DAYS

| No. | TEST NAME | TEST MATERIAL | MODEL | METHOD | PASS/FAIL-COMMENTS |
|---|---|---|---|---|---|
| 11 | Systemic Toxicity - Intramuscular Implantation | a. Final product (rabbit specific) b. Rabbit DBM powder alone Using Direct Contact Implantation Low (high clinical dose, 1× @ 3.8 g/rabbit @ approx 1 g/kg) and High dose (5× high clinical dose) implantation | Rabbit N = 4 for each dose @ each time point N = 3 DBM powder controls @ each time point Surgical implantation along vertebral column and along ribs for high dose | Sacrifice time points at 7, 14, 28, 60 and 90 days subject to absorption profile. Blood and urine at 72 hours. Blood and urine analysis with histology (liver and kidney); Evaluation for gross anatomical lesions | Pass Histopathology - No evidence of systemic toxicity No evidence of carrier at 7 days Termination of study at 60 days - No changes in hematology or clinical chemistry values; No evidence of systemic toxicity; Evidence of ectopic bone formation |
| 12 | Femoral Defect | Final Formulation | Rat | 12 Weeks; Histology and X-rays | Radiographic evidence of bone formation |

Biocompatibility of DBM with a starch stabilizer. Clearance studies confirmed the removal of DBM with a starch stabilizer carrier from the implant site in less than 30 days, classifying it as a class B tissue/bone implant category for ISO 10993 biocompatibility studies. Four evaluation tests for consideration for Class B tissue/bone implant category are listed in the ISO guidelines. They are: cytotoxicity, sensitization, implantation and genotoxicity. Acute systemic toxicity may also apply in specific cases. In addition to the suggested four tests, a total of nine additional safety, biocompatibility, and efficacy studies were performed (including Example 7). These studies are summarized in the table above.

Local Reactions

A. Acute intracutaneous injection, and acute muscle implantation studies were performed. The intracutaneous studies involved both saline and cottonseed oil extracts of a starch stabilizer. DBM with a starch stabilizer prepared with Rabbit DBM was used for muscle implantation. DBM with a starch stabilizer produced minimal irritation in both studies, being deemed a non-irritant when compared to the positive control in the muscle implantation and having a primary index characterization of negligible when administered as an intracutaneous extract. Intramuscularly applied DBM without starch carrier, was found to be a moderate irritant.

B. Cytotoxicity and Genotoxicity. Extracts of a starch stabilizer demonstrated no ability to induce cell lysis or bacterial mutagenicity. The cell lysis study employed a saline extract of DBM with a starch stabilizer. The genotoxicity studies utilized both saline and DMSO extracts tested on two bacterial species: S. typhimurium and E. coli.

C. Hemolysis and Pyrogenicity. Saline extracts of a starch stabilizer were deemed to be non-pyrogenic and non-hemolytic. Body temperatures in rabbits injected with saline extracts of DBM with a starch stabilizer gave no indication of pyrogenicity, and the extract produced a hemolytic index of 0 when added to anticoagulated pooled rabbit blood.

D. Sensitization. Extracts of the carrier showed no evidence of delayed dermal contact sensitization. This study employed a saline and cottonseed oil extracts of the carrier. Guinea pigs received an intradermal injection of the extracts and, following a recovery period, were subsequently challenged with a patch of the extract material.

E. DBM with a starch stabilizer Systemic Safety/Tox. No evidence of toxicity was observed in studies in which DBM with a starch stabilizer (rabbit DBM) was implanted intramuscularly (high dose also had subcutaneous, see below) in the paravertebral muscle, and animals monitored for 60 days. In these studies, rabbits were implanted with either approximately 3.5 cc (low dose) or 17.5 cc (high dose) of DBM with a starch stabilizer (~1.1 gm/cc). The doses on a gm per kilogram basis (~1.3 gm/kg; ~6.41 gm/kg) are approximately equivalent to 5.6× and 28× average human implantation dose (15 cc/70 kg or 0.23 gm/kg) respectively. In the case of the high dose, due to space limitations in the paravertebral implant site, only 3.5 cc of DBM with a starch stabilizer were implanted paravertebrally and the remaining 14 cc were implanted subcutaneously in the dorsal thorax.

Necropsy results for the test animals failed to show any treatment effect. Blood chemistries and urinalysis values all fell within the normal range, with the exception of serum alkaline phosphatase which was expected to increase due to the induction of ectopic bone formation in response to DBM with a starch stabilizer.

Example 9

Assaying Osteoinductivity of Test Materials

Objective: The goal of this Example is to assess the characteristics of various potential Protective Agents, and particularly to identify those with no negative impact on osteoinductivity. Preferably, the Protective Agents are easy to handle, irrigatable, non-toxic, degradable, and moldable (preferred consistency resembles plumber's putty).

Methods and Materials: This study is conducted using an athymic (nude) rat model. Preferably, a single DBM preparation is utilized in all formulations. Potential Protective Agent materials are sterilized by irradiation. Various Test Compositions, and control DBM, are implanted into animals, 6–8 sites per material. Each animal received bilateral intramuscular implantations into the hindlimbs Each Test Composition contains 40 mg DBM per bone site. The volume can vary depending on the nature of the carrier.

Results: This protocol was applied to four different Test Compositions, plus control DBM. The Test Compositions were implanted into 30 animals; DBM was implanted into 8 individual animals. Protective Agents were sterilized by autoclaving. The following Protective Agent Solutions were prepared:

| | Modified Starch Solution Preparation | |
|---|---|---|
| Name | Ingredients | Sterilization |
| E | 8% Starch, 1.6 g B980, 18.4 g DI water | Autoclave for 40 minutes |
| F | 8% Starch, 18.4% glycerol: 1.6 g B980 + 18.4 g 20% glycerol | Autoclave for 40 minutes |
| G | 8% Starch, 28.5% Maltrin 180: 2.8 g Starch + 22.2 g DI water | Autoclave for 40 minutes before addition of 10 g Maltrin M180 |
| H | 8% Starch, 12.7% glycerol, 28.5% Maltrin 180: 2.8 g Starch + 22.2 g 20% glycerol solution | Autoclave for 40 minutes before addition of 10 g Maltrin M180 |

The following Test Composition formulations were prepared:

| | Implant Preparation | |
|---|---|---|
| Name | Composition | Recipe |
| E | 8% Starch (n = 8) | 0.4 g of DBM powder mixed with 0.80 g of solution E. Mix thoroughly. |
| F | 8% Starch, 18.4% glycerol (n = 8) | 0.4 g of DBM powder mixed with 0.80 g of solution F. Mix thoroughly. |
| G | 8% Starch, 28.5% Maltrin 180 (n = 8) | 0.4 g of DBM powder mixed with 0.73 g of solution G. Mix thoroughly. |
| H | 8% Starch, 12.7% glycerol, 28.5% Maltrin 180 (n = 8) | 0.4 g of DBM powder mixed with 0.73 g of solution H. Mix thoroughly |
| Control | Human Powder (HDBM) | |

In addition, as a positive control in every animal, RDBM was placed in the left pectoralis.

Results:

| Implant Material | Mean | SD |
|---|---|---|
| HDBM - Control Human Pool KF-135-040501-10 | 2.9 | 1.0 |
| Sample E | 3.4 | 0.9 |
| Sample F | 3.8 | 0.5 |

-continued

| Implant Material | Mean | SD |
|---|---|---|
| Sample G | 3.6 | 0.8 |
| Sample H | 3.3 | 1.2 |

Conclusion: No Test Composition had a negative impact on osteoinductivity.

Example 10

Osteoinduction in a Rabbit Model

Introduction and methods: Fifty-five male New Zealand White rabbits were assigned to three treatment groups. Test article was prepared as described in Example 3. Those animals assigned to the Low Dose treatment group (n=20) received 3.5 ml of the test article in the right paravertebral muscle following a protocol specified procedure. Animals assigned to the High Dose treatment group (n=20) received 3.5 ml of the test article in the right paravertebral muscle and 7.0 ml of the test article in the subcutaneous tissue of each side of the dorsal thoracic area. The animals assigned to the Control treatment group (n=15) were implanted with 3.5 ml of control article (rehydrated DBM powder) in the right paravertebral muscle. At 7, 14, and 28 days post-implantation, four animals from the Low and High Dose treatment groups and three animals from the Control groups were humanely sacrificed. At 60 days post-implantation, the remaining animals were sacrificed (eight from the Low and High Dose test groups and six from the Control treatment group). The implant sites were collected from each rabbit and fixed in 10% neutral buffered formalin (NBF). The test and control implant sites from the 60 days post-implantation study interval were placed in decalcification solutions for 3 days after adequate formalin fixation. All tissue samples were processed using standard histological techniques, sectioned at 5 μm, and stained with hematoxylin and eosin.

Results: Osteoinduction was noted in the subcutaneous and intramuscular implant sites for the test article and in the intramuscular site for the control DBM (no subcutaneous implantation at 28 days post-implantation). New bone was characterized histologically by being slightly more eosinophilic than the demineralized bone components of the test and control articles. The new trabeculae were lined by plump (active) osteoblasts, osteogenic precursors, osteoid, and poorly mineralized osteoid. In many cases there were osteocytes present and some evidence of osteonal remodeling. In some cases cartilage was present. At 60 days post-implantation, the new bone was similarly characterized, but associated with increased thickness, remodeling, and frequently loose fibrovascular stroma (morphologically the same as observed in bone marrow) containing hematopoietic tissue was observed between the trabeculae. Subjectively, the test article had a greater degree of bone formation in the muscle implant sites than the control article. The amount of cartilage present varied between the implant sites. This variation was most likely due to differences in the microenvironment for those individual implants. The precursor cells involved in new bone formation are pluripotential and under certain microenvironmental conditions will form fibrous tissue, cartilage, or bone. The cartilage within the implant sites undergoes endochondral ossification and becomes bone. Any differences in the tissue response, bone formation, or cartilage formation between the test article implanted within the subcutaneous tissue and that implanted in muscle were due to anatomical and microenvironmental differences between the two tissues. Bone formation was noted for both the test and control article implant sites 28 days post-implantation. The amount and maturity of the bone (as evident by the amount of remodeling and the presence of loose fibrovascular stroma and hematopoietic tissue) was greatly increased at 60 days for the test article.

possessing stronger heparin-binding epitopes at the N-termini compared with the wild type BMP. The heparin-binding site enhances binding to the ECM increasing local residence time of the BMP so that the potential for interaction with the appropriate cells in vivo is maximized (Kubler et al. "EHBMP-2. Initial BMP analog with osteoinductive properties" *Mund Kiefer Gesichtschir.* 3 Suppl 1:S134–9, 1999; incorporated herein by reference).

| Treatment Group | Presence of New Bone and Cartilage by Treatment Group and Time Post-Implantation | | | |
|---|---|---|---|---|
| | 7 Days Post-Implantation Bone/Cartilage | 14 Days Post-Implantation | 28 Days Post-Implantation | 60 Days Post-Implantation |
| High Dose Muscle | 0/0 (n = 4) | 0/0 (n = 4) | 2.0/1.5 (n = 4) | 3.5/0.0 (n = 8) |
| Subcutaneous | 0/0 (n = 8) | 0/0 (n = 8) | 1.4/1.5 (n = 8) | 2.7/0.9 (n = 15) |
| Low Dose Muscle | 0/0 (n = 4) | 0/0 (n = 4) | 2.3/0.8 (n = 4) | 4.0/0.4 (n = 5) |
| Control Muscle | 0/0 (n = 4) | 0/0 (n = 4) | 0.7/0.7 (n = 4) | 2.5/0.2 (n = 6) |

The ratings in the table above were based on a 0–4 scale with 0 being 0% of implant area occupied by new (viable) bone/cartilage; 1 being 1–25% of implant area occupied by new (viable) bone/cartilage; 2 being 26–50% of implant area occupied by new (viable) bone/cartilage; 3 being 51–75% of implant area occupied by new (viable) bone/cartilage; and 4 being 76–100% of implant area occupied by new (viable) bone/cartilage.

Example 11

Terminal Sterilization

This example describes a terminal sterilization method which minimizes osteoinductivity loss in the inventive preparations.

The inventive DBM preparations are produced in a clean room environment from human tissue. The finished implants are placed in individual tray packages.

Each tray is placed in an Audionvac sealing apparatus (Audion Electro B. V., Weesp-Holland) which is supplied with a cylinder consisting of 50/50 hydrogen/argon gas. Before the tray packages are sealed, they are evacuated and backfilled with the gas mixture twice. Following sealing, the gas mixture remains in each tray package.

The packaged implants are then sealed packages and then treated with 15 KGy gamma radiation from a cobalt 60 source to reduce the bioburden of the implants to the desired level.

Example 12

Comparing Osteoinductivity of DBM preparations to BMP and/or Other Growth Factors.

In the series of studies presented here, hybrid recombinant human BMPs (hybrid rhBMPs, hrhBMPs) were prepared The aim of the studies was to compare the osteoinductive potential of hybrid rhBMP-2x (hrhBMP-2x) with wild-type BMP-2 (rhBMP-2) to determine whether a synergistic potential existed when hrhBMP-2x was combined with a demineralized bone matrix or a devitalized (inactivated bone matrix).

Methods

To assess the osteoinductive activity of the hybrid rhBMP-2x, 1, 5, and 10 µg hrhBMP-2x were placed onto 200 mg osteoinductive human demineralized bone fiber (DBF) matrix and implanted heterotopically in athymic rats for 21 days (n=6 per group). The DBF matrix was prepared so that the osteoinductive potential was approximately 50% of that usually seen so that differences between treated and untreated DBM were evident. Controls consisted of osteoinductive human DBF matrix alone, inactivated human DBF matrix alone ("devitalized", GuHCl extracted) and inactivated human DBF combined with 1, 5, and 10 µg hrhBMP-2x, active and inactivated matrix with 5 µg wild-type BMP-2. All samples were measured histologically using a 5-point scoring system (score 4=>75% of the cross-sectional area of the implant with evidence of bone formation, 3=51–75%, 2=26–50%, 1=1–25%, 0=no bone formation) (Edwards J T, Diegmann M H, Scarborough N L. Osteoinduction of human demineralized bone: characterization in a rat model. *Clin. Orthop.* 357:219–28, 1998; incorporated herein by reference).

Results

Histological scoring as described in the methods section was inadequate for scoring most of the samples that contained a morphogen. The devitalized sample alone (inactive DBF matrix) scored 0; devitalized+1 µg hrh-BMP-2x scored 0.8±0.4; DBF matrix scored 2.5±0.8; all other samples scored 4.

To further distinguish the extent of development of the nodules, a qualitative scoring system was devised to determine the vascularity of the sample and residual DBF remaining in the sample. The following scales were used:

Vascularity (bloody marrow): none=0; minor=1; few vessels, small vessels=2; moderate cellularity and vessel size=3; extensive cellularity, large vessels=4

Residual DBF: none=0; minor=1; low=2; moderate=3, extensive=4

The active DBF matrix treated with hrhBMP-2× produced a more differentiated nodule with little residual DBM present, extensive new bone formation and highly developed vasculature which was not evident in the devitalized group even at the highest concentration of morphogen. The devitalized carrier can be compared to the collagen sponge— essentially an inert, 3-dimensional structure to support bone growth. The wild-type rhBMP-2 produced a well developed vasculature and marrow however, the residual bone content was far greater that the active DBF counterpart.

Conclusion:

The results show that the modified hrhBMP-2× possessed stronger osteoinductive properties than its corresponding wild type. Ossification was accelerated and the induced bone tissue showed a denser structure. Synergistic results were obtained when hrhBMP-2× was combined with active DBF matrix and not devitalized DBF. The most likely explanation for these findings is the longer half-life of the hrhBMPs-2× at the implantation site. The persistence of the growth factor at the site allowed for longer interaction time with local cells rather than leaching into the surrounding tissues resulting in ectopic bone formation sites. An active matrix substantially increased the osteoinductive properties of the exogenously added growth factor presumably due to the combined interactions of many growth factors already present in demineralized bone (Kubler et al. "Allogenic bone and cartilage morphogenesis. Rat BMP in vivo and in vitro" *J. Craniomaxillofac. Surg.* 19(7):283–8, 1991; Kubler et al. "Effect of different factors on the bone forming properties of recombinant BMPs" *Mund Kiefer Gesichtschir.* 4 Suppl 2:S465–9, 2000; each of which is incorporated herein by reference).

Example 13

Process of Making a Species-Specific Osteoimplant with Defined Dimensions.

Long bones from human Rhesus Monkey, canine, and rabbit were used to prepare species-specific solid formed implant matrices. Bones were aseptically cleaned. The cortical bone was processed in the bone milling apparatus described in U.S. Pat. No. 5,607,269, incorporated herein by reference, to yield about 65 grams of elongate bone fibers. The elongate bone fibers were placed in a reactor and allowed to soak for about 5–10 minutes in 0.6 N HCl plus 20–2000 ppm nonionic surfactant solution. Following drainage of the HCl/surfactant, 0.6 N HCl at 15 ml per gram of total bone was introduced into the reactor along with the elongate bone fibers. The reaction proceeded for about 40–50 minutes. Following drainage through a sieve, the resulting demineralized elongate bone fibers were rinsed three times with sterile, deionized water at 15 ml per gram of total bone, being replaced at 15-minute intervals. Following drainage of the water, the bone fibers were covered in alcohol and allowed to soak for at least 30 minutes. The alcohol was then drained and the bone fibers were rinsed with sterile, deionized water. The bone fibers were then contacted with a mixture of about 4.5 ml glycerol per gram of dry bone fibers and about 10.5 ml sterile deionized water per gram of dry bone fibers s for at least 60 minutes. Excess liquid was drained and the resulting liquid composition containing approximately 11% (w/v) demineralized, elongate bone fibers was transferred to a 11 cm×11 cm mold containing a lid having a plurality of protruding indentations (approximately 1.5 cm×3.5 cm in width and length, and 4 mm in depth), the lid was gently placed on the mold such that the indentations became immersed into the fibers to exert as little pressure on the composition as possible. The dimensions of the protrusions can be made specific for the size of the osteoimplant required for the animal model of interest. The resulting cut pieces had dimensions of 4.5 cm in length, 2.5 cm in width and about 8 mm in height (or thickness) with trough dimensions 3.5 cm in length, 1 cm in width and depth of the of 4 mm. The mold was then placed in an oven at 46° C. for 4 hours. The composition was then frozen overnight at −70° C. and then lyophilized for 48 hours. Following lyophilization, the mold was disassembled and the sponge-like formed composition was cut into individual pieces that contained troughs.

The resulting composition was cohesive, flexible, sponge-like with an obvious continuous three-dimensional structure with visible open pores, had a defined shape including the indentations made by the lid protrusions, did not require rehydration before use, but was rapidly hydratable and retained its shape once wetted with fluids and freezing was not required for storage.

Example 14

Method for Fabricating a Partially Embedded DBM/Polymer Composite

The following method is used to produce a demineralized bone matrix partially embedded in a resorbable polymer. Such partially embedded DBMs provide an initial level of osteoinductivity from the non-embedded DBM portion, and then a continuous source of un-degraded active DBM as the polymer degrades with time. The method is particularly well suited for embedding DBM in tyrosine polycarbonate DT (Integra life sciences) and poly (L-lactide-co-D, L-lactide 70/30) (Boehringer Ingelheim). This device has particular application in posterior lateral spine fusion, where it can be placed within the lateral gutter to promote intertransverse process bone formation. The method can be used to half embed an appropriately shaped matrix produced by the method described in Example 10 above, or alternatively, a collection of demineralized cortical bone fibers, where the fibers, are cut approximately 1 inch in length and arranged in a cylindrical bundle with the long axes of the fibers substantially parallel with one another can be partially embedded by this method.

A stainless steel adjustable diameter circular clamp, approximately ½ inch in height is used to hold the ground polymer, along with the lower portion of the demineralized bone. The fiber bundle or matrix sample is centered in the clamp, leaving space around the inside periphery of the clamp to receive the ground polymer material. Heat is then applied to the underside of the clamp until the polymer has melted. The clamp is then tightened (diameter reduced) while the polymer is still flowable, forcing the polymer to flow into the lower part of the fiber bundle. The polymeric material is then allowed to cool and the clamp removed, embedding the lower portion of the fibers in the solid polymer.

In preferred embodiments resorbable polymers are employed. Temperatures are used which melt the polymer to a suitable viscosity to allow the melted polymer to flow in and around the demineralized bone. Most often the temperature employed will be from about 0 to about 15 degrees above the glass transition temperature of the polymer. Since the biological activity of DBM may degrade if maintained at temperatures above 60° C. for significant periods of times, the preferred polymers will have glass transition temperatures lower than 100° C. preferably lower than 80° C. and most preferable below 60° C. For tyrosine polycarbonate DT a temperature of 115° C. for 10 minutes is employed. For poly (L-lactide-co-D, L-lactide 70/30) 70° C. is suitable. This method is also applicable if a suitable polymer solvent is used instead of heat to facilitate polymer flow.

Example 15

DBM Preparation Comprising a Mixture of Stabilized DBMs with a Prolonged Half-life Diffusion Barrier Two demineralized bone formulations are prepared:

Demineralized bone preparation #1. DBM is prepared from about 150–1000 micron bone particles demineralized, lyophilized and then pre-swollen with 100% glycerol, excess glycerol is removed by filtration. Lactomer 9-1, a caprolactone glycoilide & calcium stearoyl lactylate (Tyco Inc. North Haven, Conn.) is mixed 10:1 by weight to homogeneity with the DBM. The mixture is melt cast in a mold at 70° C. Following cooling, the polymer DBM monolith is pulverized in a cryomill and sieved to a particle size of about 130–1200 microns.

Demineralized bone preparation #2: A lecithin based DBM preparation is prepared according to the method of Han et al "Synergistic Effects of Lecithin and Human DBM on Bone Induction in Nude Rats" Abstract from the 28th Annual Meeting of the Society for Biomaterials (2002) incorporated herein by reference. Briefly, Pospholipon 90G, (American Lecithin Company) is mixed with demineralized bone at a weight ration of between 40% lecithin: 60% DBM to 60% lecithin:40% DBM A third starch based demineralized bone is prepared according to Example 2 with the exception that only one third of the total demineralized bone was added to the starch carrier. In place of the remaining two thirds of demineralized bone, is added equal amounts demineralized bone from preparations #1 & #2 of this Example. The composition is then mixed to form the implant preparation.

Example 16

Competitive Substrate

Poly-L-lysine may be used as a competitive inhibitor for serine protease enzymes. This example describes the preparation of demineralized bone incorporating poly-L-lysine. Poly-L-lysine (10–300 kD) is prepared in 1 mM HCL in a range of concentrations from about 1–10 mg/ml. Demineralized bone is prepared. Following final washing it is mixed with the poly-L-lysine solution in one of 5 concentrations to form a thick slurry (~0.33gm/mL). The demineralized bone/substrate mixture is lyophilized to dryness. The demineralized bone thus prepared is used directly or formulated with a carrier.

Example 17

A Fatty Acid/Starch Diffusion Barrier Matrix

Demineralized bone is prepared as described in example 14 with the modification that the polymer/DBM preparation is omitted, being replaced by an equal weight of the lecithin preparation.

Example 18

Osteoinduction of DBM Composition in an Athymic Rat Model

The purpose of this Example is to evaluate the osteoinductive potential of DBM compositions using a heterotopic osteoinductive 28-day implant model (Edwards et al., Clin. Orthop. Rel. Res. 357:219–228, 1998; Urist, Science 150: 893–899, 1965; each of which is incorporated by reference). The DBM composition includes cuboidal shaped DBM particles in combination with DBM fibers (See U.S. Ser. No. 60/159,774, filed Oct. 15, 1999; WO0232348; each of which is included herein by reference). Chondrocytes are the predominant cell type in the cube of the DBM following 28-day implantation. This study extends the implant time to 49 days to look evidence of continued bone remodeling within the demineralized cortical cube.

Materials and Methods: Equal volumes of crunch samples weighing approximately 600 mg were packaged in 2.5 ml blunt tipped syringes. Eighteen female athymic rats were obtained from Harlan Sprague Dawley Inc. (Indianapolis, Ind.). Animals weights at the time of surgery ranged between 186 g and 236 g. 28-day and 49-day implants were evaluated.

The implant sites were assessed histologically. The fiber component was scored independently of the cubes and was assigned a numerical score based on a 5 point semiquantitative scale based on percent of fiber area involved in new bone formation. The cube portion was assigned a score based on the percent of central Haversian systems involved in new bone formation.

Results: New bone, marrow, and adipocytes were present throughout the fiber portion of the nodules. Chondrocytes were present within the central Haversian systems at all time points. At the 28-day time point, the mean osteoinductive score for the fiber portion was 3.1±0.5 for the fiber portion 89.8±5.8% of the Haversian canals occupied in the cube portion. Cubes were surrounded by new bone or marrow and pockets of chondrocytes occurred within and between cubes.

The mean osteoinductive score at the 49-day time point was 3.5±0.5 for the fiber portion with 98.1±2.4% of the Haversian canals occupied in the cubes. The notable differences from the 28-day samples included almost complete remodeling of the fiber portion, large pockets of chondrocytes and areas of new bone within the cubes and remodeling at the edges of the cube.

Conclusions: The cortical cubes play an important role in the osteoinductivity of the DBM composition. The cubes are cut from cortical bone and the central Haversian canals provide a natural porosity. Cartilage persisting after 28 days coincides with a delay in bone formation presumably due to the delayed vascular ingrowth. At 49 days, the cubes showed evidence of remodeling albeit slower than the fibers. Bone remodeling occurred faster on the external surfaces compared to internal surfaces. The cubes continue to provide the important support matrix and osteoinductive signal required for normal bone formation throughout the healing response.

Example 19

Establishment of Handling Characteristics for Inventive Compositions

The following example describes the addition of demineralized bone to an inventive stabilizing agent and/or diffusion barrier to produce a formable osteoinductive implant composition. The example describes the establishment of an appropriate carrier viscosity, mixing the carrier with DBM, and adjustment of the final handling properties of the competed composition.

Carrier Viscosity. The inventive starch based compositions were prepared as described in Example 3, with a variety of starch to water ratios ranging from about 5% to about 45%. The starch powders was mixed with water and the mixture was autoclaved to produce a sterile hydrated starch preparation. The autoclaved starch was then tested for viscosity. Starch formulations with viscosities within the range of 5000 to 20000 sCp were used to prepared DBM compositions.

A Brookfield Viscometer (HB-DV III+) with the appropriate sample adaptor (SSA27/13RPY s/n RP66162 with spindle #27), supported by Rheocalc32 software was used to determine the viscosity of the starch carrier.

Mixing of carrier and DBM. The starch carrier with a viscosity of approximately 5000 sCpi was mixed with varying quantities of DBM (from about 10% to about 50% DBM by weight) to produce a composition with a consistency similar to that of modeling clay or bread dough. Variations employing lesser amounts of DBM resulted in a composition with a cohesive yet almost flowable product. Formulations employing more DBM produced a product with a very stiff consistency, and formulations with high levels of DBM became crumbly and fragmented while mixing. These formulations were then quantitatively assessed for handling as described below.

Assay for composition handling properties. The following method was used to establish consistency in handling properties of the inventive compositions. Compositions employing starch-based carriers with penetration resistance values of 25–120N were considered acceptable, with values of 30–90N representing a more preferable range and values between 40–65 N being even more preferable.

A 1" diameter×9" long threaded (14 tpi) push rod was mounted to the actuator of a MTS 858 Bionix Test System fitted with a 1 kN force transducer. A piece of 1.5" diameter× 6" length PVC pipe was centered vertically on the force transducer and a large weigh boat was placed underneath it to catch the extruded bone formulation. A 1" I.D.×0.5" thick spacer was placed on top of the PVC tubing and 7.00 g of bone mixture was weighed into a 5 cc syringe and loaded into the tip of the syringe using a clean, dry 5 cc syringe plunger with the tip removed just below the o-ring to create a flat surface. The loaded syringe was placed vertically into the spacer/PVC pipe assembly with the plunger facing up. The whole assembly (PVC pipe, spacer, and syringe) was centered on the load cell directly under the push rod. The center of the plunger was lined up with the center of the push rod. The 1 kN load range was used for the first test of each new bone formulation. When the maximum load required to extrude the bone mixture was less than 90N, then the 100N load range was used during subsequent tests to achieve a higher degree of accuracy. The test sample was preloaded under load control to 5N, the displacement was zeroed, and the test was executed. Bone formulations were extruded at a rate of 5 mm/min to a maximum displacement of 20 mm in compression. The average maximum force required to extrude each bone formulation was then determined.

Example 20

Detection of Amylase Sensitivity

This example describes the assessment of amylase resistance for starch-based stabilizers and diffusion barriers (carriers). Increasing the amylase resistance of a starch-based carrier increases the effective residence time of the carrier following implantation and therefore enhances the stabilizing effect of the carrier.

Quantification of resistant starches requires the use of pancreatic a amylase and amyloglucosidase that effectively detect the breakdown of amylase-resistant starches to glucose.

The breakdown of the starch and starch/lipid compositions of Examples 3, 9, 15, and 17 as well as new candidate amylase resistant starches and modified starches, is monitored using the resistant starch assay kit from Megazyme International Ireland Ltd. (Amyloglucosidase α-Amylase Method AOAC Method 996.11, AACC Method 76.13, ICC Standard Method No. 168). Formulations with slowest breakdown will generally have the longest stabilization effect in vivo.

Example 21

Starch/Lipid Carrier Compositions

The following compositions were prepared in a similar fashion to those described in Example 3, 9, 15, and 17. Carriers were autoclaved for 20 minutes to sterilize them prior to mixing with DBM.

Combination #1—Carrier 1 consisted of about 8% Penford Maps 281 and 5% Lecithin with the remainder being water.

Combination #2—Carrier 2 consisted of about 8% Penford Maps 281 and 15% Lecithin with the remainder being water.

Combination #3—Carrier 3 consisted of about 6% GPC B980 and 5% Lecithin with the remainder being water.

Combination #4—Carrier 4 consisted of about, 6% GPC B980 and 15% Lecithin with the remainder being water.

Each of the four carrier combinations were mixed with human DBM to yield a bone content of about 25%. These bone mixtures were then tested for osteoinductivity as previously described in Example 6.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

Appendix A

The biologically active agents that in the DBM compositions of the present invention are any substances having biological activity, including small molecules, chemical compounds, proteins, polypeptides, polynucleotides, nucleoproteins, polysaccharides, glycoproteins, lipoproteins, and synthetic and biologically engineered analogs thereof.

Examples of biologically active compounds that might be utilized in a DBM composition of the invention include literally any hydrophilic or hydrophobic biologically active compound. Preferably, though not necessarily, the drug is one that has already been deemed safe and effective for use by the appropriate governmental agency or body. For example, drugs for human use listed by the FDA under 21 C.F.R. 330.5, 331 through 361; 440-460; drugs for veterinary use listed by the FDA under 21 C.F.R. 500-582, incorporated herein by reference, are all considered acceptable for use in the present novel polymer networks.

Drugs that are not themselves liquid at body temperature can be incorporated into DBM and other polymers. Moreover, peptides and proteins which may normally be lysed by tissue-activated enzymes such as peptidases, can be passively protected in polymers or DBM as well.

The term "biologically active compound" includes pharmacologically active substances that produce a local or systemic effect in animals, plants, or viruses. The term thus means any substance intended for use in the diagnosis, cure, mitigation, treatment or prevention of disease or in the enhancement of desirable physical or mental development and conditions in an animal, plant, or virus. The term "animal" used herein is taken to mean mammals, such as primates, including humans, sheep, horses, cattle, pigs, dogs, cats, rats, mice; birds; reptiles; fish; insects; arachnids; protists (e.g. protozoa); and prokaryotic bacteria. The term "plant" means higher plants (angiosperms, gymnosperms), fungi, and prokaryotic blue-green "algae" ( i.e. cyanobacteria).

The biologically active compound may be any substance having biological activity, including proteins, polypeptides, polynucleotides, nucleoproteins, polysaccharides, glycoproteins, lipoproteins, and synthetic and biologically engineered analogs thereof. The term "protein" is art-recognized and for purposes of this invention also encompasses peptides. The proteins or peptides may be any biologically active protein or peptide, naturally occurring or synthetic.

Examples of proteins include antibodies, enzymes, steroids, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide-T, thyrocalcitonin, parathyroid hormone, glucagon, vasopressin, oxytocin, angiotensin I and II, bradykinin, kallidin, adrenocorticotropic hormone, thyroid stimulating hormone, insulin, glucagon and the numerous analogues and congeners of the foregoing molecules.

Classes of biologically active compounds which can be loaded into crosslinked gels using the methods of this invention include, but are not limited to, anti-AIDS substances, anti-cancer substances, antibiotics, immunosuppressants (*e.g.*, cyclosporine) anti-viral substances, enzyme inhibitors, neurotoxins, opioids, hypnotics, antihistamines, lubricants tranquilizers, anti-convulsants, muscle relaxants and anti-Parkinson substances, anti-spasmodics and muscle contractants, miotics and anti-cholinergics, anti-glaucoma compounds, anti-parasite and/or anti-protozoal compounds, anti-hypertensives, analgesics, anti-pyretics and anti-inflammatory agents such as NSAIDs, local anesthetics, ophthalmics, prostaglandins, anti-depressants, anti-psychotic substances, anti-emetics, imaging agents, specific targeting agents, neurotransmitters, proteins, cell response modifiers, and vaccines.

A more complete listing of classes of compounds suitable for loading into polymers using the present methods may be found in the *Pharmazeutische Wirkstoffe* (Von Kleemann et al. (eds) Stuttgart/New York, 1987, incorporated herein by reference). Examples of particular biologically active substances are presented below:

Anti-AIDS substances are substances used to treat or prevent Autoimmune Deficiency Syndrome (AIDS). Examples of such substances include CD4, 3'-azido-3'-deoxythymidine (AZT), 9-(2-hydroxyethoxymethyl)-guanine acyclovir(), phosphonoformic acid, 1-adamantanamine, peptide T, and 2',3' dideoxycytidine.

Anti-cancer substances are substances used to treat or prevent cancer. Examples of such substances include methotrexate, cisplatin, prednisone, hydroxyprogesterone, medroxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busulfan, carmustine, lomusline, dacarbazine (DTIC: dimethyltriazenomidazolecarboxamide), methotrexate, fluorouracil, 5-fluorouracil, cytarabine, cytosine arabinoxide, mercaptopurine, 6-mercaptopurine, thioguanine.

Antibiotics are art recognized and are substances which inhibit the growth of or kill microorganisms. Antibiotics can be produced synthetically or by microorganisms. Examples of antibiotics include penicillin, tetracycline, chloramphenicol, minocycline, doxycycline, vanomycin, bacitracin, kanamycin, neomycin, gentamycin, erythromicin and cephalosporins.

Anti-viral agents are substances capable of destroying or suppressing the replication of viruses. Examples of anti-viral agents include a-methyl-P-adamantane methylamine, 1,-D-ribofuranosyl-1,2,4-triazole-3 carboxamide, 9-[2-hydroxy-ethoxy]methylguanine, adamantanamine, 5-iodo-2'-deoxyuridine, trifluorothymidine, interferon, and adenine arabinoside.

Enzyme inhibitors are substances which inhibit an enzymatic reaction. Examples of enzyme inhibitors include edrophonium chloride, N-methylphysostigmine, neostigmine bromide, physostigmine sulfate, tacrine HCl, tacrine,1-hydroxy maleate, iodotubercidin, p-bromotetramisole, 10-(alpha-diethylaminopropionyl)- phenothiazine hydrochloride, calmidazolium chloride, hemicholinium-3, 3,5-dinitrocatechol, diacylglycerol kinase inhibitor I, diacylglycerol kinase inhibitor II, 3-phenylpropargylamine, $N^6$-monomethyl-L-arginine acetate, carbidopa, 3-hydroxybenzylhydrazine HCl, hydralazine HCl, clorgyline HCl, deprenyl HCl,L(-)-, deprenyl HCl,D(+)-, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate,R(+)-, p-aminoglutethimide tartrate,S(-)-, 3-iodotyrosine, alpha-methyltyrosine,L-, alpha -methyltyrosine,D L-, acetazolamide, dichlorphenamide, 6-hydroxy-2-benzothiazolesulfonamide, and allopurinol.

Neurotoxins are substances which have a toxic effect on the nervous system, e.g. nerve cells. Neurotoxins include adrenergic neurotoxins, cholinergic neurotoxins, dopaminergic neurotoxins, and other neurotoxins. Examples of adrenergic neurotoxins include N-(2-chloroethyl)-N-ethyl-2-bromobenzylamine hydrochloride. Examples of cholinergic neurotoxins include acetylethylcholine mustard hydrochloride. Examples of dopaminergic neurotoxins include 6-hydroxydopamine HBr, 1-methyl-4-(2-methylphenyl)-1,2,3,6- tetrahydro-pyridine hydrochloride, 1-methyl-4-phenyl-2,3- dihydropyridinium perchlorate, N-methyl-4-phenyl-1,2,5,6-tetrahydropyridine HCl, 1-methyl-4-phenylpyridinium iodide.

Opioids are substances having opiate like effects that are not derived from opium. Opioids include opioid agonists and opioid antagonists. Opioid agonists include codeine sulfate, fentanyl citrate, hydrocodone bitartrate, loperamide HCl, morphine sulfate, noscapine, norcodeine, normorphine, thebaine. Opioid antagonists include nor-binaltorphimine HCl, buprenorphine, chlornaltrexamine 2HCl, funaltrexamione HCl, nalbuphine HCl, nalorphine HCl, naloxone HCl, naloxonazine, naltrexone HCl, and naltrindole HCl.

Hypnotics are substances which produce a hypnotic effect. Hypnotics include pentobarbital sodium, phenobarbital, secobarbital, thiopental and mixtures, thereof, heterocyclic hypnotics, dioxopiperidines, glutarimides, diethyl isovaleramide, a-bromoisovaleryl urea, urethanes and disulfanes.

Antihistamines are substances which competitively inhibit the effects of histamines. Examples include pyrilamine, chlorpheniramine, tetrahydrazoline, and the like.

Lubricants are substances that increase the lubricity of the environment into which they are delivered. Examples of biologically active lubricants include water and saline.

Tranquilizers are substances which provide a tranquilizing effect. Examples of tranquilizers include chloropromazine, promazine, fluphenzaine, reserpine, deserpidine, and meprobamate.

Anti-convulsants are substances which have an effect of preventing, reducing, or eliminating convulsions. Examples of such agents include primidone, phenytoin, valproate, Chk and ethosuximide.

Muscle relaxants and anti-Parkinson agents are agents which relax muscles or reduce or eliminate symptoms associated with Parkinson's disease. Examples of such agents include mephenesin, methocarbomal, cyclobenzaprine hydrochloride, trihexylphenidyl hydrochloride, levodopa/carbidopa, and biperiden.

Anti-spasmodics and muscle contractants are substances capable of preventing or relieving muscle spasms or contractions. Examples of such agents include atropine, scopolamine, oxyphenonium, and papaverine.

Miotics and anti-cholinergics are compounds which cause bronchodilation. Examples include echothiophate, pilocarpine, physostigmine salicylate, diisopropylfluorophosphate, epinephrine, neostigmine, carbachol, methacholine, bethanechol, and the like.

Anti-glaucoma compounds include betaxalol, pilocarpine, timolol, timolol salts, and combinations of timolol, and/or its salts, with pilocarpine.

Anti-parasitic, -protozoal and -fungals include ivermectin, pyrimethamine, trisulfapyrimidine, clindamycin, amphotericin B, nystatin, flucytosine, natamycin, and miconazole.

Anti-hypertensives are substances capable of counteracting high blood pressure. Examples of such substances include alpha-methyldopa and the pivaloyloxyethyl ester of alpha-methyldopa.

Analgesics are substances capable of preventing, reducing, or relieving pain. Examples of analgesics include morphine sulfate, codeine sulfate, meperidine, and nalorphine.

Anti-pyretics are substances capable of relieving or reducing fever and anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances which have an anesthetic effect in a localized region. Examples of such anesthetics include procaine, lidocain, tetracaine and dibucaine.

Ophthalmics include diagnostic agents such as sodium fluorescein, rose bengal, methacholine, adrenaline, cocaine, and atropine. Ophthalmic surgical additives include alpha-chymotrypsin and hyaluronidase.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Anti-psychotic substances are substances which modify psychotic behavior. Examples of such agents include phenothiazines, butyrophenones and thioxanthenes.

Anti-emetics are substances which prevent or alleviate nausea or vomiting. An example of such a substance includes dramamine.

Imaging agents are agents capable of imaging a desired site, e.g. tumor, *in vivo*. Examples of imaging agents include substances having a label which is detectable *in vivo*, e.g. antibodies attached to fluorescent labels. The term antibody includes whole antibodies or fragments thereof.

Specific targeting agents include agents capable of delivering a therapeutic agent to a desired site, e.g. tumor, and providing a therapeutic effect. Examples of targeting agents include agents which can carry toxins or other agents which provide beneficial effects. The targeting agent can be an antibody linked to a toxin, e.g. ricin A or an antibody linked to a drug.

Neurotransmitters are substances which are released from a neuron on excitation and travel to either inhibit or excite a target cell. Examples of neurotransmitters include dopamine, serotonin, q-aminobutyric acid, norepinephrine, histamine, acetylcholine, and epinephrine.

Cell response modifiers are chemotactic factors such as platelet-derived growth factor (PDGF). Other chemotactic factors include neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor, and bone growth/cartilage-inducing factor (alpha and beta), or other bone morphogenetic protein.

Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenetic proteins.

The invention claimed is:

1. An osteoinductive composition for implantation at a bone defect site, the osteoinductive composition comprising osteoinductive demineralized bone matrix in a carrier of hydrated polysaccharide, the type and quantity of polysaccharide present in the carrier being sufficient, upon hydration, of imparting flowability to the composition, said composition having an osteoinductive activity of at least 1 as measured by an athymic rat model assay, wherein the polysaccharide comprises starch.

* * * * *